United States Patent [19]
Kyle

[11] Patent Number: 5,658,767
[45] Date of Patent: Aug. 19, 1997

[54] ARACHIDONIC ACID AND METHODS FOR THE PRODUCTION AND USE THEREOF

[75] Inventor: David J. Kyle, Catonsville, Md.

[73] Assignee: Martek Corporation, Columbia, Md.

[21] Appl. No.: 367,881

[22] Filed: Jan. 3, 1995

Related U.S. Application Data

[63] Continuation-in-part of Ser. No. 202,878, Feb. 28, 1994, abandoned, which is a continuation of Ser. No. 35,507, Mar. 22, 1993, abandoned, which is a continuation of Ser. No. 645,454, Jan. 24, 1991, abandoned.

[51] Int. Cl.$^6$ ............... A23C 9/00; A23C 11/00; C12P 7/64
[52] U.S. Cl. ............ 435/434; 426/585; 514/558; 514/560
[58] Field of Search ............... 435/134, 171; 514/558, 560; 426/585

[56] References Cited

FOREIGN PATENT DOCUMENTS

| 032423 | 9/1989 | European Pat. Off. . |
| 3603000 | 8/1987 | Germany . |
| 1196255 | 8/1989 | Japan . |
| 1215245 | 8/1989 | Japan . |
| WO9213086 | 8/1992 | WIPO . |

OTHER PUBLICATIONS

H. Yamada, et al., "Production of Dihomo-γ-linolenic Acid, Arachidonic Acid and Eicosapentaenoic Acid by Filamentous Fungi", in Kyle, et al., Ind. Apl. Single Cell Oils, 1992, pp. 118–138.

*Primary Examiner*—Blaine Lankford
*Attorney, Agent, or Firm*—Baker & Botts, L.L.P.

[57] ABSTRACT

The present invention relates to processes for the production of arachidonic acid containing oils, which preferably are substantially free of eicosapentaneoic acid. The invention also relates to compositions containing such oils, in an unmodified form, and to uses of such oils. In a preferred embodiment, *Pythium insidiosum* is cultivated, harvested and the oil is extracted, recovered, and used as an additive for infant formula. In an alternative embodiment, *Mortierella alpina* is cultivated, harvested and the oil is extracted, recovered, and used as an additive for infant formula.

52 Claims, No Drawings

ARACHIDONIC ACID AND METHODS FOR THE PRODUCTION AND USE THEREOF

This application is a Continuation-in-Part of U.S. application Ser. No. 08/202,878, filed Feb. 28, 1994, now abandoned, which is a Continuation of U.S. application Ser. No. 08/035,507, filed Mar. 22, 1993, now abandoned, which is a Continuation of U.S. application Ser. No. 07/645,454, filed Jan. 24, 1991, now abandoned.

The text of each of these prior applications are incorporated herein by reference, in their entirety.

FIELD OF THE INVENTION

This invention relates to the production of arachidonic acid, to compositions containing arachidonic acid and to uses thereof.

BACKGROUND OF THE INVENTION

Arachidonic acid (ARA) is a long chain polyunsaturated fatty acid (PUFA) of the omega-6 class (5, 8, 11, 14-eicosatetraenoic acid, i.e., 20:4). ARA is the most abundant $C_{20}$ PUFA in the human body. It is particularly prevalent in organ, muscle and blood tissues, serving a major role as a structural lipid associated predominantly with phospholipids in blood, liver, muscle and other major organ systems. In addition to its primary role as a structural lipid, ARA also is the direct precursor for a number of circulating eieosenoids such as prostaglandin $E_2$ ($PGE_2$), prostacyclin $I_2$ ($PGI_2$), thromboxane $A_2$ ($T_xA_2$), and leukotirenes $B_4$ ($LTB_4$) and $C_4$ ($LTC_4$). These eicosenoids exhibit regulatory effects on lipoprotein metabolism, blood theology, vascular tone, leucocyte function and platelet activation.

Despite its importance to human metabolism, ARA cannot be synthesized in humans de novo. ARA is synthesized by the elongation and desaturation of linoleic acid (LOA), an essential fatty acid. This process requires the presence of the enzyme Δ6-desaturase, an enzyme present in the human body in low levels, Burre et al., *Lipids*, 25:354–356 (1990). Accordingly, most ARA must be provided in the diet, and this is especially important during times of very rapid body growth, such as infancy.

During the first year of its life, an infant can double or triple its weight. Consequently, elevated levels of dietary ARA are required. To satisfy this increased demand, human breast milk contains high levels of ARA. Sanders et al., *Am. J. Clin. Nutr.*, 31:805–813 (1978). ARA is the most prevalent $C_{20}$ PUFA in breast milk. Of those mothers, especially vegetarians, who do breast-feed their infants, many would benefit from additional dietary ARA. However, many mothers do not breast feed their infants, or do not breast feed for the entire period of rapid infant growth, choosing instead to utilize an infant formula.

No commercial infant formulas known to Applicant contain ARA in triglyceride form. U.S. Pat. No. 4,670,285 (Clandinin et al.), incorporated herein by reference, discloses the infant's requirement for fatty acids including ARA. To provide these fatty acids, Clandinin et al. suggest a blend of egg yolk, fish oil or red blood cell phospholipids and vegetable oils as the fat component of a proposed infant formula. However, fish oil contain high quantities of eicosapentaneoic acid (EPA). EPA is known to depress ARA synthesis in infants. Carlson, et al., *INFORM.*, 1:306 (1990). Thus, it would be desirable to be able to provide ARA without also providing additional EPA. Furthermore, egg yolks contain a relatively low concentration of ARA, such that Clandinin et al.'s mixture is not economically viable.

Because ARA is present in animal, but not vegetable, oils, its production in commercial quantities has remained a desirable, but elusive, goal. Shinmen, et al., *Microbiol. Biotech.* 31:11–16 (1989), have reported the production of ARA by an isolated fungus, *Mortierella alpina*, using conventional stirred tank fermentation. (See also Japanese Patent 1,215,245 to Shinmen et al.). After culturing, the organisms are harvested, dried and their lipids extracted from the fungal biomass with an organic solvent and the lipids chemically (covalently) modified. For example, the lipid mixture is hydrolyzed or converted to ethyl esters and then combined with cyclodextrin prior to use as a dietary supplement. Shinmen et al. do not disclose or suggest the administration of unmodified microbial oils.

*Porphyridium cruentum*, a red microalgae, can be grown in ponds in large quantities and has a lipid content which can contain up to 40% ARA. Ahem, et al. *Biotech. Bioeng.* 25:1057–1070 (1983). Unfortunately, the ARA is primarily associated with galactolipids, a complex polar lipid not present in breast milk. Thus, not only is the total usable ARA produced a fraction of one percent of the biomass, but the form of the ARA is not suitable for use as an additive to infant formula without further modification.

U.S. Pat. No. 4,870,011 (Suzuki et al.) discloses a method for obtaining lipids such as γ-linolenic acid from fungi of the genus Mortierella. The γ-linolenic acid is purified from the mixture of lipids contained in the fungi.

DE 3603000A1 (Milupa) discloses a highly polyunsaturated acid fat mixture and its use as the fat component of an infant formula. The fat mixture has a high content of ARA and docosahexanoic (DHA) acids in a ratio of 2.5:1 respectively, as well as a high content of cholesterol. Sources of the fatty acids are listed as being certain types of macroalgae, fish oils, organ fats from beef and pork or highly refined egg yolk off. A source of the DHA and ARA is said to be macroalgae of the phaecophyte and rhodophyte types. There is no suggestion to use any microbes as a source of oil. Algal and fish oils also typically include EPA which depresses ARA synthesis in vivo. Additionally, highly refined egg yolk oil is not an economical source of ARA. Moreover, there is no disclosure therein of an ARA-concentrated additive for supplementing pre-existing infant formula.

Accordingly, there remains a need for an economical, commercially feasible method of producing ARA, preferably without concomitant production of EPA. It is an object of the present invention to satisfy that need.

It is a further object of the invention to provide an additive, and a source for that additive, for use in an infant formula such that the ARA levels in the formula approximate those levels in human breast milk.

It is an additional object of this invention to provide an ARA-containing fungal oil for use in enteral, parenteral or dermal products.

SUMMARY OF THE INVENTION

This invention relates to the production and use of arachidonic acid containing fungal oil (ARASCO) and to compositions containing such oils. The oil can be referred to as a single cell oil. Fungi are cultivated under oil-producing conditions, harvested and the oil extracted and recovered. The oil, without further chemical modification, can be used directly to provide supplemental ARA to persons requiring such, including newborn infants, pregnant or nursing women or persons exhibiting ARA-deficient pathologies. Advantages of the invention include its ease of production, and high purity, and lack of detectable amounts of EPA.

DETAILED DESCRIPTION OF THE PREFERRED EMBODIMENTS

"ARA" and "EPA" are also used herein to refer to residues of arachidonic acid and eicosapentaneoic acid, respectively, where the residues are esterified to glycerol as part of a fatty acyl triglyceride or a phospholipid. As used herein, a composition is "essentially free of EPA" when the residual amount of EPA in the composition is less than the amount that would depress ARA synthesis when the composition is used as a nutritional supplement. The present invention succeeds in providing an economical source of arachidonic acid (ARA).

In one embodiment, this invention relates to a method for the production of an arachidonic acid-containing fungal oil (ARASCO) which is substantially free of eicosapentaneoic acid (EPA). As used herein, "substantially free" means that the EPA is present in less than about one fifth of the amount of ARA in the oil. This oil, a single cell oil, can be administered directly, in an unmodified form. As used herein "unmodified" means that the chemical properties of the fatty acids, or the oils themselves, have not been covalently altered. Thus, for example, a temporary modification to the ARASCO or ARA which could be reversed following uptake of the off would not be beyond the scope of this invention.

Unmodified fungal oils according to this invention provide triglycerides in which a relatively high proportion of the fatty acid residues are ARA, and the ratio of ARA residues to EPA residues is also high (at least 5:1, preferably at least 20:1, w/w). Such an oil from natural sources has not been described prior to the present invention. While triglycerides with such composition may be chemically synthesized (e.g., by esterifying free fatty acid mixtures high in ARA or transesterifying with ethyl esters of such a fatty acid mixture), the manipulation of the fatty acid mixture (e.g., purification, esterification, etc.) may introduce unwanted side-products. In contrast, the method of this invention provides triglycerides having the desired composition by extraction from natural sources.

found that *P. insidiosum* produces ARA without concomitant production of EPA. As with fish oils, high EPA levels in dietary supplements result in a depression of the ability to form ARA from dietary linoleic acid (LOA). Accordingly, while those fungal species producing both ARA and EPA can be utilized in the process of this invention, it is preferable to use species which do not produce significant quantities of EPA. Such preferred species include *Pythium insidiosum* and *Mortierella alpina*. Both species are available commercially and are on deposit with the American Type Culture Collective in Rockville, Md., having accession numbers 28251 and 42430, respectively. *P. insidiosum* and *M. alpina* have been used as representative fungal species throughout this disclosure. Of course, other fungal species which produce triglyceride containing ARA and reduced EPA as described herein are also contemplated within this invention.

One of the significant problems which an embodiment of the present invention overcomes, is the depression of ARA biosynthesis in infants caused by the presence of enhanced dietary levels of EPA. This problem can be corrected by providing ARA for use in infant formula at levels substantially similar to those found in human breast milk. Typically in human breast milk, the ratio of ARA:EPA is about 20:1 respectively. The present invention specifically contemplates any microbial oil which provides a sufficient amount of ARA to overcome the negative effects of dietary EPA. Preferably, the use of the ARA-containing oil will result in an ARA:EPA ratio of at least about 5:1. More preferably, the ratio will be at least about 10:1 and, most preferably, it will be at least about 20:1. As can be seen, the higher the amount of ARA in the end product, with respect to the amount of EPA, the more desirable is the result.

In a process of the present invention, the fungi are cultivated under suitable ARA-containing oil producing cultivating conditions. In general, techniques of fungal cultivation are well known to those of skill in the art and those techniques can be applied to the present inventive process. For example, cultivation of an inoculating amount of fungus can occur in submerged culture in shake flasks. The flasks are provided with a growth medium, seeded with fungal

TABLE 1

Fatty Acid Composition of Several Fungal Species

| Species | 14:0 | 16:0 | 16:1 | 18:1 | 18:2 | 18:3 | 20:4 | 20:5 | Total Fat |
|---|---|---|---|---|---|---|---|---|---|
| *Mortierella alpina* | — | 8.2 | — | 33.5 | 16.3 | 23.3 | 13.0 | — | 3.0 |
| *Mortierella elongata* | 2.0 | 13.2 | — | 26.6 | 11.9 | 13.2 | 13.8 | 2.4 | 4.0 |
| *Mortierella isabellina* | 0.3 | 15.7 | 0.8 | 55.8 | 11.1 | 9.0 | — | — | 7.3 |
| *Saprolegnia parasitica* | 7.4 | 19.1 | 1.9 | 6.3 | 24.5 | 12.5 | 10.5 | 10.5 | 9.3 |
| *Pythium catenulatum* | 6.5 | 9.9 | 10.3 | 21.2 | 18.5 | 3.5 | 13.4 | 10.9 | 5.0 |
| *Pythium coloratum* | 13.6 | 9.9 | — | 14.7 | 10.9 | 2.5 | 24.3 | 21.7 | 2.2 |
| *Pythium gracile* | 14.7 | 9.1 | 2.2 | 14.8 | 12.6 | 3.6 | 22.1 | 5.7 | 4.5 |
| *Pythium irregulare* | 10.3 | 15.4 | 6.9 | 12.3 | 21.0 | 3.9 | 10.6 | 12.4 | 11.9 |
| *Pythium ultimum* | 9.5 | 16.7 | 10.5 | 17.1 | 20.7 | 1.3 | 9.0 | 6.9 | 13.3 |
| *Pythium insidiosum* | 9.5 | 11.4 | 12.1 | 1.0 | 8.3 | 9.3 | 31.9 | — | 2.8 |

Of those fungal species which previously have had their fatty acids characterized, it has been found that most do not make ARA. Weete, J. D., *Fungal Lipid Biochemistry*, Plenum Press, New York. (1974). Of those species which do make ARA, many, including all previously characterized Pythium species, produce significant quantities of eicosapentaenoic acid (EPA) in addition to ARA. Table 1 sets forth the fatty acid profile of *P. insidiosum* as well as the fatty acid profile of other species of fungi. Unexpectedly, it has been mycelium, and grown on a reciprocating shaker for about three to four days.

The composition of the growth medium can vary but always contains carbon and nitrogen sources. A preferred carbon source is glucose, amounts of which can range from about 10–100 grams glucose per liter of growth medium. Typically about 15 grams/liter are utilized for shaker flask culture. The amount can be varied depending upon the desired density of the final culture. Other carbon sources which can be used include molasses, high fructose corn syrup, hydrolyzed starch or any other low cost conventional carbon source used in fermentation processes. Additionally, lactose can be provided as a carbon source for *P. insidiosum*. Thus, whey permeate, which is high in lactose and is a very low cost carbon source, can be used as a substrate. Suitable amounts of these carbon sources can readily be determined by those of skill in the art. Usually, additional carbon needs to be added during the course of the cultivation. This is because the organisms use so much carbon that adding it all in a batch mode could prove unwieldy.

Nitrogen typically is provided in the form of yeast extract at a concentration of from about 2 to about 15 grams extract per liter of growth medium. Preferably, about four grams per liter are provided. Other nitrogen sources can be used, including peptone, tryptone, cornsteep liquor, soy flour, hydrolyzed vegetable protein, etc. The amount to be added of these sources can easily be determined by those of skill in the art. Nitrogen can be added in a batch mode, i.e. all at one time prior to cultivation.

After cultivation for 3–4 days at a suitable temperature, typically about 25°–30° C., an amount of fungi has grown which is sufficient for use as an inoculum in a conventional stirred tank fermentor (STF). Such fermentors are known to those of skill in the art and are commercially available. Fermentation can be carried out in batch, fed-batch, or continuous fermentation modes. Preferably, the STF is equipped with a marine impeller, although a Rushton-type turbine impeller can also be used.

The fermentor is prepared by adding the desired carbon and nitrogen sources. For example, a 1.5 liter fermentor can be prepared by mixing about 50 grams of glucose and about 15 grams of yeast extract per liter of tap water. As previously discussed, other carbon or nitrogen sources or mixtures thereof can be used.

The reactor containing the nutrient solution should be sterilized by, for example, heating prior to inoculation. After cooling to about 30° C., the inoculum can be added, and cultivation initiated. Gas exchange is provided by air sparging. The air sparging rate can vary, but preferably is adjusted to from about 0.5 to about 4.0 VVM (volume of air per volume of fermentor per minute). Preferably the dissolved oxygen level is kept at from about 10% to about 50% of the air saturation value of the solution. Accordingly, adjustments in the sparge rate may be required during cultivation. Agitation is desirable. The agitation is provided by the impeller. Agitation tip speed preferably is set within the range of from about 50 cm/see to about 500 cm/see, preferably from about 100 to 200 cm/sec.

In general, the amount of inoculum can vary. Typically, from about 2% to about 10% by volume of inoculum can be used. Preferably, in a fermentor seed train about 5% by volume of inoculum can be used.

Nutrient levels should be monitored. When glucose levels drop below 5 g/l, additional glucose should be added. A typical cultivation cycle utilizes about 100 grams of glucose and about 15 grams of yeast extract per liter. It is desirable to deplete the nitrogen during the course of the cultivation as this enhances oil production by the fungi. This is especially true when *M. alpina* is used as the production organism.

In a particularly preferred embodiment, *Mortierella alpina* with high oil content including high levels of ARA may be cultured in a fermentor using very high nutrient levels. It has been unexpectedly discovered that levels of nitrogen-containing nutrient in excess of that provided by 15 grams/liter of yeast extract may be added at the beginning of the fermentation, so long as the total mount of carbon-containing nutrient added during the fermentation is comparably high. The total amount of carbon nutrient, preferably fed continuously or intermittently for the first 25–50% of the fermentation time course, or in aliquots at multiple time points over the same portion of the time course, will preferably be equivalent to 75–300 grams of glucose per liter of culture medium (C:N ratio ≧5:1, expressed as w/w glucose:yeast extract). In an especially preferred mode, the nitrogen nutrient is soy flour, added at a level of about 16 grams per liter of medium, and the carbon nutrient is present initially at a level equivalent to about 80 grams of glucose or greater. When using high levels of carbon and nitrogen nutrients, it is preferable to sterilize solutions containing the two nutrient solutions separately.

Occasionally, the culture will produce an excessive quantity of foam. Optionally, an antifoaming agent, such as those known to those of skill in the art, e.g. Mazu 310®, can be added to prevent foam.

The temperature of cultivation can vary. However, those fungi which produce both ARA and EPA tend to produce less EPA and more ARA when cultivated at higher temperatures. For example, when *Mortierella alpina* is cultivated at less than 18° C., it begins to produce EPA. Thus it is preferable to maintain the temperature at a level which induces the preferential production of ARA. Suitable temperatures are typically from about 25° C. to about 30° C.

Preferably, cultivation continues until a desired biomass density is achieved. A desirable biomass is about 25 g/l of the organism. Such a biomass typically is attained within 48–72 hours after inoculation. At this time, the organisms typically contain about 5–40% complex lipids, i.e. oil, of which about 10–40% is ARA, and can be harvested.

Fungal fermentation for ARA production according to this invention may be carried out in fermentation medium with pH between about 5 and 8. However, yields of biomass, oil and ARA from cultures of *M. alpina* can be enhanced by profiling the pH of the medium, rather than allowing uncontrolled pH rise. Yields may also be enhanced by maintaining high oxygen levels during the fermentation. These modifications of fermentation procedure are especially effective when using high nutrient levels in the fermentor.

When the initial nitrogen nutrient level exceeds the equivalent of about 15 grams of yeast extract per liter, and/or the carbon nutrient level exceeds the equivalent of about 150 grams glucose per liter, growth of fungi may be inhibited. This growth inhibition may be overcome by fed batch fermentation, for example by dividing the total nutrient for the fermentation into aliquots which are fed into the fermentor sequentially, once part or all of the nutrient supplied by the previous aliquot has been metabolized. It has been unexpectedly discovered that growth inhibition can be mitigated by pH profiling of the fermentation, by maintaining high oxygen tension in the fermentor, or both.

It has been discovered that fermentation of *M. alpina* in high nutrient media at low pH (pH=5–6) results in enhanced biomass growth (and also in increased oil yield). However, the oil produced under these conditions has lower levels of ARA residues in the oil. Contrariwise, fermentation at high pH (pH=7–7.5) results in increased levels of ARA in the oil, but poorer growth. In a preferred mode, the fermentation method of this invention involves pH profiling wherein the pH is low during the early stages of the fermentation and high during the late stages. Early stages include periods of rapid (exponential) growth during which nutrients are rapidly metabolized; late stages include the stationary phase, when cell division is arrested, usually due to insufficient amounts of one or more nutrients, and the production of ARA-rich oil is enhanced. Profiling can be done by controlling fermentor pH at levels that are adjusted in two or more steps spaced over the fermentation period.

It has likewise been discovered that maintaining the dissolved oxygen content of the medium (D.O.) at high levels (e.g., $\geq 40\%$ of air saturation level) will result in relief of the growth inhibition by high nutrient levels and/or increase the relative level of ARA residues in the oil. The D.O. may be maintained at a high level by increasing vessel pressure (forcing more air into the fermentor head space), increasing agitation (e.g., increasing the impeller tip speed), and increasing aeration (i.e., increasing the amount of air passing through the fermentor in a given time, usually expressed as increase in vvm, volumes of air per fermentor volume per minute) and/or by increasing the $O_2$ content of the sparge gas. Fermentation under these conditions has been found to increase carbon utilization, resulting in higher final biomass concentration and greater productivity of ARA-rich oil in the fermentor.

In a particularly preferred embodiment, the fermentation medium contains carbon nutrient equivalent to $\geq 80$ g/L glucose and nitrogen nutrient equivalent to $\geq 16$ g/L yeast extract, and the medium is adjusted to pH between 5 and 6 subsequent to sterilization. After inoculation, the pH of the medium is controlled at or slightly above its initial level. Once the carbon nutrient level has dropped to $\leq 60$ grams glucose equivalent/liter (usually about 48 hours), the setpoint for pH control is changed to about pH$\geq 6$. At or about the time when the oxygen uptake rate (and/or the carbon dioxide evolution rate, CER) reaches its maximum (usually after about 72 hours), the setpoint is raised to pH between 6.5 and 7 (usually incrementally, e.g., at a rate of about 0.1 pH units per hour). The pH is then controlled to keep it below about pH=7-7.5 for the final stages of the fermentation.

For this embodiment, dissolved oxygen level in the medium (D.O.) is maintained near or above 40% of air saturation level, preferably by sequentially increasing vessel pressure to 11 psi, increasing agitation to the equivalent of about 300 cm/sec impeller tip speed, and increasing aeration to about 0.5 volumes of air per fermentor volume per minute. After a period of rapid growth and high $O_2$ uptake by the fermentation, growth (and $O_2$ uptake) will decrease. Agitation/aeration can be reduced at this point, so long as D.O. is maintained at a high level, usually above about 40% air saturation.

By optimizing the fermentation of *M. alpina* as described herein, it is possible to obtain very high yields of biomass containing 20–60% oil in the biomass, where 25–70% by weight of the oil is ARA residues in triglyceride form. The biomass (and oil) may be harvested as described herein. Preferably, biomass will be harvested from the fermentor within 48 hours of reaching maximum productivity, measured as grams ARA/L/day.

Harvesting can be done by any suitable method such as, for example, filtration, centrifugation, or spray drying. Because of lower cost, filtration may be preferred.

After harvesting, the mycelial cake can be extracted. The mycelial cake refers to the collection of biomass resulting after harvest. The cake can be loose or pressed, crumbled or uncrumbled. Optionally, the cake can have any residual water removed, as by vacuum drying, fluid bed drying, spray drying or lyophilization, prior to extraction. If this option is selected, it is preferable to use nonpolar solvents to extract the ARA-containing oil. While any non-polar extract is suitable, hexane is preferred.

In a preferred embodiment, oil is extracted from the dried biomass by wet grinding or percolation with virgin hexane. Solvent is usually added at a solvent-to-biomass ratio of about 5:1 (w/w). After wet grinding, solids are separated from the extract by decanting or centrifugation. It is advantageous to maintain the solvent-containing extract (miscella) anaerobically to avoid oxidation of the unsaturated fatty acid residues in the oil. Miscella is desolventized to produce a crude fungal oil.

Crude oil extracted from fungal biomass with non-polar solvents can be cloudy, particularly when the biomass is ground, because grinding may release fine particles such as cell wall fragments and soluble polysaccharides. Clarification of such cloudy oil may be accomplished by dissolving the crude oil in more polar solvents, such as acetone or alcohol. In a preferred embodiment, crude oil extract of fungal mycelia is further clarified by acetone extraction/precipitation. An acetone miscella is prepared by adding acetone to cloudy crude oil extract (preferably to a level of about 20% oil; i.e., about 4 volumes of acetone per volume of crude oil), mixing thoroughly and allowing the mixture to stand for a period sufficient for precipitation of the free particles (usually about an hour room temperature). The oil-containing acetone miscella is clarified by centrifugation and/or filtration, and then desolventized to produce acetone-clarified fungal oil. Acetone-clarified fungal oil is preferred for further processing (e.g., degumming, bleaching and deodorizing by conventional techniques) because the fines produced during extraction of the fungal biomass will interfere with the refining processes if not removed in the acetone step.

Another preferred embodiment involves the counter-current extraction of dry biomass, which, may be carried out in commercially available extraction units, for example, those manufactured by Crown Ironworks (Crown Mark IV) or French, Inc., that are not generally used to extract vegetable oils, but were designed to extract dirt and soil. Although extraction efficiencies are not as high without the regrinding of the biomass, the counter current extraction procedure has the advantage of producing fewer "fines" thereby reducing the technical difficulty in recovering a clear refined oil.

Alternatively, the wet cake (which typically contains about 30–50% solids) can be crumbled and extracted directly using polar solvents such as ethanol or isopropyl alcohol, or supercritical fluid extraction with solvents such as $CO_2$ or NO. Preferably, the cakes are crumbled prior to extraction. Advantageously, the present invention permits the economical use of supercritical fluid extraction techniques. McHugh, et al., *Supercritical Fluid Extraction*, Butterworth (1986). Such techniques are known to those of skill in the art and include those presently applied, for example, to decaffeinate coffee beans.

A preferable method of aqueous extraction involves mixing the mycelial biomass with the polar solvent isopropyl alcohol in a suitable reaction kettle. Such kettles are known. The use of three to six parts of solvent per part of biomass is desired. Most preferably, the mixing is done under nitrogen or in the presence of antioxidants to prevent the oxidation of the ARA in the lipid extract. As used herein "lipid extract", "oil", "lipid complex" and "fungal oil" are used interchangeably.

After extracting, the mixture can be filtered to remove the biomass from the solvent containing the lipid extract. At this point, the biomass can be recovered and used as a food supplement. As used herein, "food supplement" means feed or an additive to be mixed with typical feed, such as grain, etc., that can be provided to animals.

The solvent is separated from the lipid extract and also can be recovered for reuse, as by evaporation into a suitable collector, leaving what is referred to herein as the "crude oil." Use of isopropyl alcohol as the solvent desirably results in the removal of any residual water from the crude oil, as the evaporation removes the water/isopropyl alcohol azeotrope which has spontaneously formed.

While the crude oil can be used without further treatment, it also can be further purified. Processes such as those used in the preparation of lecithin from vegetable products, and known to those of skill in the art, can be used in this additional purification step. Such processes do not chemically or covalently modify the ARA-containing lipids or the ARA itself.

Yields vary, but typically are about 5 grams of ARA-containing phospholipid per 100 grams of dried mycelia. In the case of *M. alpina*, an additional 10–50 grams of triglyceride per 100 grams of dry mycelia can be obtained. Either the crude oil or the refined product can be used for administration to humans. Both shall be included within the definition of ARASCO as used herein.

A most preferred object of the invention is to provide an additive for use with human infant formulas, such that the concentration of ARA in such formula closely approximates the concentration of ARA in human breast milk. Table 2 compares the composition of the fatty acids in ARASCO with those in breast milk and infant formula lacking and containing ARASCO.

TABLE 2

Fatty Acid Composition of Fungal Oil Products And Mother's Milk

| Fatty Acid | ARASCO | Infant Formula[1] | Formula + Oil | Breast Milk |
|---|---|---|---|---|
| 8.0 | — | 24.1 | 23.6 | 0.35 |
| 10:0 | — | 17.7 | 17.3 | 1.39 |
| 12:0 | — | 14.9 | 14.6 | 6.99 |
| 14:0 | 4.6 | 5.8 | 5.8 | 7.96 |
| 16:0 | 16.0 | 6.8 | 7.0 | 19.80 |
| 16:1 | 3.2 | 0.2 | 0.3 | 3.20 |
| 18:0 | — | 2.3 | 2.3 | 5.91 |
| 18:1 | 26.4 | 10.0 | 10.3 | 34.82 |
| 18:2n6 | 9.9 | 17.4 | 17.3 | 16.00 |
| 18:3n3 | 4.1 | 0.9 | 1.0 | 0.62 |
| 20:1 | 2.2 | 0.1 | 0.14 | 1.10 |
| 20:2n6 | — | — | — | 0.61 |
| 20:3n6 | 1.4 | — | 0.03 | 0.42 |
| 20:4n6 | 32.0 | — | 0.64 | 0.59 |
| 20:5n3 | — | — | — | 0.03 |
| 22:1 | — | — | — | 0.10 |
| 22:4n6 | — | — | — | 0.21 |
| 22:5n6 | — | — | — | 0.22 |
| 22:6n3 | — | — | — | 0.19 |

[1]Simopoulis, A., Omega-3 Fatty Acids in Health and Disease, pp. 115–156 (1990).

As can be seen, the amount of ARA present in the infant formula supplemented by ARASCO closely approximates the ARA levels in human breast milk. Additionally, the total fatty acid composition of the infant formula has not been significantly altered by the addition of the ARASCO. Typically, between about 50 to about 1000 mg of ARASCO per liter of infant formula can be used. The specific amount of ARASCO required depends upon the ARA content. This can vary from about 10 to about 70% of the fatty acids in the oil. However, typically the ARA content is about 30–50%.

When the ARA content is about 30% an especially preferred supplementation rate is about 600 to 700 mg of ARASCO per liter of infant formula. Such a rate dilutes the pre-existing fat components of an infant formula such as Similac® (Ross Laboratories, Columbus, Ohio) by only one part ARASCO to fifty parts formula oils. Preferably, the ARASCO is substantially free of EPA.

When *Pythium insidiosum* is used in the described process, the extracted ARA-containing oil is predominantly phospholipid. However, it has been discovered that a significant amount of triglyceride which is high in ARA residues may also be recovered from *P. insidiosum* cultured as described herein. When *Mortierella alpina* is used in this process, the ARA-containing oil is predominantly triglyceride. Both forms of ARASCO are useful as additives to infant formula. The former not only provides the formula with ARA, but also with an emulsifier, i.e., phosphatidyl choline, which is commonly added to commercial formulas. The oil from *M. alpina* is likely to be more economical to produce.

The ARA-containing oil of the present invention has many uses in addition to its use as an additive for infant formula. As known to those of skill in the art, there are many pathologies associated with ARA deficiencies, such as marasmus (Vajreswari, et al., *Metabolism* 39:779–782 (1990)) or atopic diseases (Melnik, B., *Monatsschr. Kinderheilta*, 138:162–166 (1990)). In one embodiment of the present invention, those pathologies are treated by administering a pharmaceutically effective mount of the oil of the present invention. The oil can be administered enterally, topically or parenterally, as selected by the provider of health care.

Encapsulation, as known by those of skill in the art, is an effective method of enteral administration. Capsules containing the fungal oil can be administered to those persons requiring or desiring dietary supplementation of ARA. Such a method is particularly effective for administering ARA to pregnant or nursing women.

In instances where ARASCO is being administered to combat ARA deficiency associated pathologies, a pharmaceutically effective amount should be administered. This amount can be determined by those of skill in the art without undue experimentation.

Another embodiment of the present invention entails cosmetic compositions containing ARASCO. Cosmetic compositions refer to those compounds applied as cosmetics. A preferred example of such a composition is a wrinkle cream. Such cosmetic compositions provide an effective means of topically applying ARA to skin to assist in maintaining skin tone.

The invention having been generally described, the following specific non-limiting examples are set forth to further illustrate the invention.

EXAMPLE 1

Preparation of *P. insidiosum* lipid and addition to infant formula

In an 80 liter (gross volume) fermentor, 51 liters of tap water, 1.2 kg glucose, 240 grams of yeast extract and 15 ml of MAZU 210S® antifoam were combined. The fermentor was sterilized at 121° C. for 45 minutes. An additional 5 liters of condensate water were added during the sterilization process. The pH was adjusted to 6.2, and approximately 1 liter of inoculum (at a cell density of 5–10 g/l) of *Pythium insidiosum* (ATCC #28251) then was added. The agitation rate was adjusted to 125 RPM (250 cm/sec tip speed) and the aeration rate was set al 1 SCMF (standard cubic feet per minute). At hour 24 in the operation the aeration rate was increased to 3 SCFM. At hour 28 an additional 2 liters of 50% glucose syrup (1 kg glucose) were added. At hour 50 the fermentor was harvested, resulting in a yield of about 2.2 kg wet weight (approximately 15 g dry weight) per liter. Harvested biomass was squeezed to a high solids cake (50 % solids) on a suction filter before freeze drying. The dried biomass was ground with a mortar and pestle and extracted with 1 liter of hexane per 200 grams of dry biomass at room temperature under continuous stirring for 2 hours. The mixture then was filtered and the filtrate evaporated to yield about 5–6 grams of crude oil per 100 grams of dry biomass. The biomass then was re. extracted with 1 liter of ethanol per 20 grams of dry biomass for 1 hour at room temperature, filtered, and the solvent evaporated yielding an additional 22 grams of crude oil per 100 grams of dry biomass. The second fraction was predominantly phospholipids whereas the first fraction contained a mixture of phospholipids and triglycerides. The combined fractions produced an oil containing about 30–35% arachidonic acid and no detectable EPA. This oil was added dropwise to the commercial infant formula product Similac® (Ross Laboratories, Columbus, Ohio) at a supplementation rate of 60 mg per liter of prepared medium.

EXAMPLE 2

Preparation of *M. alpina* lipid and addition to infant formula

*Mortierella alpina* (ATCC #42430) was grown in a 2 liter shake flask containing 1 liter of tap water and 20 grams of potato dextrose medium. The flask was under constant orbital agitation and was maintained at 25° C. for seven days. After harvesting by centrifugation, the biomass was freeze dried yielding about 8 grams of lipid-rich mycelia. The mycelia was extracted using hexane as in example #1 and about 2.4 g of crude oil resulted. This oil contains about 23% arachidonic acid and was added to the commercial formula Similac® dropwise in concentrations of 1000 mg per liter.

EXAMPLE 3

Large Scale Production of Arachadonic Acid by *M. alpina*

Inoculation fermentor containing medium GYE (50 g/L dextrose and 6 g/L Tastone 154) is inoculated with *M. alpina*. Fermentation temperature is set al 28° C., initial agitation at 130–160 cm/sec, initial vessel pressure at 6 psi, and initial aeration rate at 0.25 vvm. pH is adjusted to 5.0 presterilization, and initial fermentation pH is set to 5.5 post-sterilization. Medium is maintained at pH ≧5.5 with 8N NaOH. Oxygen level is maintained at D.O. ≧40% by adjusting agitation/aeration in the following sequence: increase vessel pressure to 11 psi; increase agitation to 175 cm/sec impeller tip speed; and increase aeration to 0.5 vvm. Foaming is controlled by addition of Dow 1520-US antifoam as needed. (Approximately 0.1 ml/L of the antifoam should be added to the medium prior to sterilization to help prevent foaming.)

Transfer inoculum from seed fermentor to main fermentor within 12 hours after pH rises above 6.0.

The main fermentor contains GYE medium (50 g/L dextrose and 6 g/L Tastone 154); glucose is sterilized separately and added to the main fermentor after sterilization. Fermentor temperature is set al 28° C., initial agitation at 160 cm/sec, initial vessel pressure at 6 psi, and initial aeration rate at 0.15 vvm. Initial pH is set to 5.5 post-sterilization, and maintained at pH≧5.5 with 8N NaOH. pH is allowed to rise during stationary phase (beginning about 24 hours after inoculation), but maintained below pH 6.8 with $H_2SO_4$ addition. Oxygen level is maintained at D.O. ≧40% by sequentially increasing vessel pressure to 11 psi, increasing agitation to 175 cm/sec impeller tip speed, and increasing aeration to 0.5 vvm. Foaming is controlled by addition of antifoam Dow 1520-US, as needed. (Approximately 0.1 ml/L of the antifoam should be added to the medium prior to sterilization to help prevent foaming).

The culture is sampled every 12 hours for biomass and fatty acid analysis, and harvest is initiated 3–4 days after pit rises to 6.5. Dry biomass density should be ≧8.5 g/L. Glucose concentration in the broth should have dropped from 50 g/L to ≦25 g/L. At harvest, the whole culture broth is passed through a basket centrifuge to separate the mycelia from the spent medium, and the biomass is dried.

EXAMPLE 4

Improved yield of Biomass from *M. alpina*—First Run

*M. alpina* was cultured in 20 L stirred tank fermentors, inoculated from shake flask culture, according to the procedure in Example 3. Culture of *M. alpina* in 65 g/L glucose (Staleydex), and 6 g/L yeast extract (Tastone 154), resulted in the production of 12 g/L biomass. The addition of an additional 6 g/L Tastone 154 at 16 hours, resulted in the production of 18 g/L biomass.

EXAMPLE 5

Improved yield of Biomass from *M. alpina*—Second Run

Experiments were carded out in an attempt to increase the biomass further by additional additions of Tastone 154. These experiments consisted of 2×20 L fermentations, of 168 hours residency. For both these fermentations, the initial glucose concentration was 100 g/L (as compared to 65 g/L for Example 4). One fermentor received 3×6 g/L additions of Tastone 154, and the other received 4×6 g/L additions. The yeast extract was made up as a concentrated solution, autoclaved, and added to the fermenter at various times post-sterilization.

To prepare the inoculum, working seeds (1 ml macerated mycelium) were inoculated into 2 flasks, each containing 50 ml of GYE medium (100 g/L Staleydex, 6 g/L Tastone 154), and grown for 4 days at 28° C. and 150 rpm. After 4 days of growth, the broth contained pelleted biomass; pellets were 2–5 mm in diameter. The growth in these flasks was slower than expected, possibly due to the higher concentration of glucose. The biomass was macerated for 2×3 secs in a Waring blender, and 25 ml of macerate was used to inoculate each of 2×2.8 L Fernbach inoculum flasks, 800 ml net volume. (In earlier experiments, 10 ml of macerate had been used. The amount of inoculum was increased, because of the lower biomass density in the seed flask, and because it was expected that growth may be slower in the Fernbachs, due to the higher glucose concentration.) The medium in the Fernbach flasks was dextrose (Staleydex) 100 g/L and yeast extract (Tastone 154), 8 g/L. The dextrose and yeast extract were autoclaved separately for 40 min. Seed fermentation temperature was maintained at 28° C. and agitation at 100 rpm to 150 rpm.

After 44 hours culture in the Fernbach flasks, the inoculum was transferred to 2×20 L fermentors. The inoculum was in the form of very loose hyphal aggregates, and the biomass density was approximately 5.2 g/L.

Fermenters at stations 14 and 15, containing 1.6 kg (10%) dextrose (Staleydex), and Mazu 204 antifoam (1.6 g, dissolved in 12.5 L R.O. $H_2O$), were sterilized for 45 min at 122° C. 800 ml of inoculum (5%) was then added to each fermentor (at 0 hours). Fermentor operating parmeters were:

temperature: 28° C., pH: controlled at 5.5 with 2N NaOH and 2N $H_2SO_4$, aeration: 0.5 vvm, back pressure: 0.2 bar, agitation (initial): 80 cm/sec, and D.O.: controlled above 40%.

Station 14: 3×6 g/L Tastone 154

Yeast extract (Tastone 154) was dissolved to a concentration of 96 g/L and autoclaved for 1 hr. Yeast extract feeds in 3×1 L mounts (1.8%), were made at 0, 20, and 26 hours.

At 15 hours, the DO dropped below 40% and agitation was increased incrementally to 175 cm/sec from 15 to 22 hours. DO was then controlled by mending the airflow with oxygen; oxygen was added to the airflow from 23 to 72 hours. Starting at 36 hours, the agitation was further increased to ensure proper mixing. By 48 hours, agitation had been increased to 200 cm/sec; by 72 hours, to 250 cm/sec; and by 80 hours, to 280 cm/sec. At 120 hours, agitation was increased to 290 cm/sec to promote adequate temperature control. At 144 hours, agitation was reduced to 280 cm/sec.

Station 15: 4×6 g/L Tastone 154

Yeast extract (Tastone 154) 384 g was dissolved in 96 g/L, and autoclaved for 1 hr. Additions of yeast extract in 4×1 L mounts (2.4%) were made at 0, 20, 26, and 32 hours.

At 16 hours, DO dropped below 40% and agitation was increased incrementally to 175 cm/sec by 23 hours. DO was then controlled above 40% by amending the airflow with oxygen; oxygen was added to the airflow from 23 to 72 hours. Starting at 36 hours, the agitation was further increased to ensure proper mixing. By 48 hours, agitation had been increased to 210 cm/sec; by 72 hours, to 260 cm/sec; and by 80 hours to 290 cm/sec. At 90 hours, the agitation was reduced to 280 cm/sec, and at 144 hours, it was reduced to 260 cm/sec.

Observations:

At inoculation, the biomass in both fermenters was in the form of very loose, feathery, hyphal aggregates. By 24 hours, pellets began to form. The pellets were small (1–3 mm), with small central cores and wide loose peripheries. At 48 hours, the pellets were larger, and better defined. By 72 hours, the peripheries were narrower, and the presence of many loose hyphal fragments indicated that the pellets were fragmenting. By 168 hours, pellet cores were 0.5 to 2 mm in diameter, the peripheries were reduced with the hyphae aggregating into thick strands, and there were many condensed hyphal aggregates.

The fermenters foamed only slightly for the first 24 hours. The amount of foaming then increased, and was controlled by manual addition of antifoam when the foam head was greater than 2–4 cm. Foaming had subsided somewhat by 48 hours, although there were sporadic outbreaks. Both fermenters foamed into the exit filters once during the course the fermentations. The fermentations required approximately 150 ml of antifoam.

Both fermenters accumulated a considerable amount of accreated biomass in the headspace. This is not an uncommon problem with mycelia fermentation in small fermentors with large surface area/volume ratio. The amount of accreated biomass in Stn 15 appeared to increase during the last 24 hours, when the lowered volume level resulted in a considerable amount of splashing (the liquid level was approaching the top impeller). The final volume in the fermenters after 168 hours was approximately 13 L.

Microscopic examination showed that, by 72 hours, much debris was present in the culture broth, and there was some evidence of damaged and atrophied fungal tips. The presence of oil droplets in the cytoplasm was demonstrated by nile red staining at 168 hours. The oil droplets were very small and numerous, in contrast to the large oil drops sometimes seen. Biomass and oil yield, along with carbon and nitrogen utilization are shown in Table 3.

TABLE 3

Fermentation Time Course

| Log Hour | Glucose (g/L) | NH3 (mM) | Dry Wt (g/L) | oil content (% dry wt) | ARA content (% of oil) | productivity (g oil/L/d) |
|---|---|---|---|---|---|---|
| | | | Stn 14 3 × 6 g/L YE | | | |
| 0 | 105.0 | 3.0 | 0.4 | | | |
| 24 | 97.4 | 5.9 | 3.3 | 4.8% | 23.5% | 0.16 |
| 48 | 73.7 | 0 | 18.3 | 7.9% | 23.4% | 0.72 |
| 72 | 60.3 | 0 | 21.0 | 14.4% | 25.4% | 1.01 |
| 96 | 48.0 | 0 | 22.3 | 18.3% | 27.5% | 1.02 |
| 120 | 40.0 | | 25.2 | 21.1% | 29.4% | 1.06 |
| 144 | 34.7 | | 26.6 | 21.8% | 30.9% | 0.97 |
| 168 | 29.0 | | 27.5 | 26.1% | 31.3% | 1.03 |
| | | | Stn 15 4 × 6 g/L YE | | | |
| 0 | 109.0 | 2.9 | 0.4 | | | |
| 24 | 103.0 | 5.1 | 3.4 | 4.3% | 21.9% | 0.15 |
| 48 | 74.1 | 0.3 | 23.6 | 6.8% | 23.1% | 0.80 |
| 72 | 51.4 | 0 | 29.8 | 10.3% | 23.9% | 1.02 |
| 96 | 40.0 | 0 | 32.7 | | | |
| 120 | 27.9 | | 31.7 | 18.2% | 26.6% | 1.15 |
| 144 | 19.8 | | 33.5 | 20.7% | 28.1% | 1.16 |
| 168 | 11.0 | | 29.9 | 21.7% | 29.9% | 0.93 |

EXAMPLE 6

Improved yield of biomass from *M. alpina*—Third Run

This set of experiments attempted to further increase the mount of product obtained by increasing the levels of phosphate and minerals. The procedure was essentially that of Example 5, except that the dextrose and Mazu 204 antifoam were dissolved in 11.5 L of R.O. $H_2O$, rather than 12.5 L, to leave room for the salt solutions which were added at 30 hours. Stn. 14 received additional Fe, Zn, and Cu; Stn 15 received additional phosphate, as well as Fe, Zn, and Cu.

Station 14: 3×6 g/L Tastone 154

Yeast extract was dissolved at 96 g/L, in 3×1 L amounts, and autoclaved for 1 hr. One liter aliquots of the yeast extract solution were added at 0, 22, and 28 hours. At 22 and 28 hours, the carbon dioxide evolution rate (CER, an indication of the metabolic rate in the fermentor) was increasing exponentially, and the fermentation had just started calling for base.

The salts feed contained:

| | |
|---|---|
| $FeCl_3$ $6H_2O$ | 480 mg |
| $ZnSO_4$ $7H_2O$ | 240 mg |
| $CuSO_4$ $5H_2O$ | 16 mg |

The $FeCl_3$ was dissolved in 1 L of 5 g/L citric acid. The remaining salts were added, and the pH adjusted with NaOH to 4.5. The solution was autoclaved for 1 hour. The salts feed was added at 30 hours.

The initial agitation rate for the fermentor was 50 cm/sec, rather than 80 cm/sec, as originally planned, because the initial level of liquid in the fermenter (13 L) resulted in top impeller being just barely submerged, and the higher agitation rate resulted in significantly more splashing. At 16 hours, the D.O. dropped below 40%, and agitation was increased incrementally to 175 cm/sec by 28 hours. D.O. was then controlled above 40% by amending the airflow with oxygen. At 46 hrs, the agitation was increased to 190 cm/sec to allow for mixing. Agitation was further increased to 200 cm/sec by 48 hours, to 220 cm/sec by 51 hours, to 235 cm/sec by 53 hours, to 250 cm/sec by 56 hours, to 260 cm/sec by 57 hours, and to 280 cm/sec at 70 hours. Even at this agitation rate (450 rpm), mixing was poor. While a minimal criteria of 'some movement' was maintained, the turnover of biomass was very slow, and some areas approached stagnation. The addition of a few drops of antifoam reduced the foam head, and removed stagnant pockets. At 116 hours, the agitation was reduced to 265 cm/sec, and at 120 hours, it was further reduced to 250 cm/sec.

The fermenter started to foam at approximately 18 hours. Foaming was controlled by manual addition of antifoam. Antifoam was first added at 20 hours. By 24 hours, the fermentation was foaming significantly, and required the regular addition of antifoam. By 72 hours, the foaming had, for the most part subsided. However, the fermentation still required the occasional addition of antifoam.

By 24 hours, the biomass was in the form of very loose pellets (1–2 mm) and loose hyphal aggregates. There was a considerable amount of cellular debris. By 48 hours, the biomass was in the form of very loose hyphal aggregates, very small pellets (1–2 mm) with very small cores and loose peripheries, and small compact pellets (1–3) without loose peripheries. By 96 hours, the biomass was in the form of compact, round pellets (1–2 mm), needle shaped pellets (less than 0.5 mm), and loose hyphal aggregates. Nile red staining at 144 hours showed the presence of many, very small oil drops in the mycelia.

Station 15: 3×6 g/L Tastone 154

Yeast extract was dissolved at 96 g/L, and autoclaved for 1 hr. The yeast extract solution was added in 3×1 L amounts at 0, 22, and 26 hours. At 22 and 26 hours, the CER was increasing exponentially, and the fermentation had just started calling for base.

| | | |
|---|---|---|
| | $KH_2PO_4$ | 77 g |
| | $FeCl_3\ 6H_2O$ | 480 mg |
| | $ZnSO_4\ 7H_2O$ | 240 mg |
| | $CuSO_4\ 5H_2O$ | 16 mg |

The $FeCl_3$ was dissolved in 500 ml of 5 g/L citric acid. The remaining salts were added, and the pH adjusted with NaOH to 4.5. The $KH_2PO_4$ was dissolved in 500 ml R.O. water. Both solutions were autoclaved for 1 hour, and then cooled to 23 C, before being combined and added to the fermentor at 30 hours.

The initial agitation rate in the fermentor was 50 cm/sec, rather than 80 cm/sec, as originally planned, because the initial level of liquid in the fermenter (13 L) resulted in top impeller being just barely submerged, and the higher agitation rate resulted in significantly more splashing. At 16 hours, the D.O. dropped below 40%, and agitation was increased incrementally to 175 cm/sec by 27 hours. D.O. was then controlled above 40% by amending the airflow with oxygen. At 41 hours, agitation was increased to 200 cm/sec, to allow for at least a minimal amount of mixing. Agitation was further increased to 220 cm/sec at 42 hrs, to 230 cm/sec at 46 hours, at 235 cm/sec at 51 hrs, and to 240 cm/sec at 70 hours. At this agitation rate (410 rpm), mixing was only poor to fair. A minimal level of biomass movement was maintained. At 80 hours, agitation was reduced to 205 cm/sec.

The fermenter started to foam at approximately 18 hours. Foaming was controlled by manual addition of antifoam. Antifoam was first added at 17 hours. By 20 hours the fermentation was foaming significantly, and it required the regular addition of antifoam. The foaming had largely subsided by 72 hours. However, the fermentation still required the occasional addition of antifoam.

By 24 hours, the biomass was in the form of very loose pellets (1–2 mm) and loose hyphal aggregates. There was a considerable amount of cellular debris. By 48 hours, the biomass was in the form of very loose hyphal aggregates, very small pellets (1–2 mm) with very small cores, and loose peripheries, and small compact pellets (1–3) without loose peripheries. By 96 hours, the biomass was in the form of round pellets, 1–2 mm in diameter, many with loose, hairy peripheries, and many loose hyphal fragments. Nile Red staining at 144 hours showed the presence of many, very small oil drops in some mycelia, and also the presence of very large oil drops throughout other mycelia.

Stn 15, which differed from Stn 14 only by the addition of phosphate, showed better mixing throughout the fermentation, at generally lower agitation rates. Stn 15 also exhibited a 'looser' biomass morphology. Biomass and oil yield, as well as carbon utilization are shown in Table 4. Greater glucose utilization (82 g/L for Stn 15 compared to 64 g/L for Stn 14), higher biomass accumulation, and presence of large oil drops in portions of the mycelia characterized the fermentor containing higher phosphate.

TABLE 4

Fermentation Time Course

| Log Hour | Glucose (g/L) | Dry Wt (g/L) | oil content (% dry wt) | ARA content (% of oil) | productivity (g oil/L/d) |
|---|---|---|---|---|---|
| | | | Stn 14 + Salts | | |
| 0 | 116.0 | 1.1 | | | |
| 24 | 101.0 | 1.8 | 1.2% | 22.2% | 0.02 |
| 48 | 84.0 | 14.3 | 6.2% | 24.7% | 0.44 |
| 72 | 60.0 | 24.5 | 10.6% | 24.2% | 0.87 |
| 96 | 45.0 | 28.2 | 15.5% | 25.3% | 1.09 |
| 120 | 34.0 | 28.9 | 18.1% | 26.6% | 1.05 |
| 144 | 27.0 | 30.8 | 20.8% | 27.2% | 1.07 |
| | | | Stn 15 + Salts + Phosphates | | |
| 0 | 113.0 | 0.4 | | | |
| 24 | 101.0 | 2.1 | 1.1% | 24.0% | 0.02 |
| 48 | 74.0 | 21.7 | 8.1% | 24.7% | 0.88 |
| 72 | 51.0 | 26.2 | 19.9% | 26.5% | 1.74 |
| 96 | 31.0 | 30.1 | 25.5% | 28.6% | |
| 120 | 18.0 | 33.8 | 31.7% | 31.4% | 2.14 |
| 144 | 6.0 | 34.5 | 36.0% | 32.9% | 2.07 |

EXAMPLE 7

Large Scale Production of *M. alpina* biomass containing Arachadonic Acid

A seed fermentor containing GYE medium (50 g/L dextrose and 6 g/L Tastone 154) is inoculated from propagation fermentor. Temperature of 28° C. is maintained and initial agitation set to 130–160 cm/see (about 43 rpm). Initial vessel pressure is 6 psi, and initial aeration rate set al 0.25 vvm. pH is adjusted to 5.0 presterilization, then initial fermentor pH is set to 5.5 post-sterilization. Oxygen level in the medium is maintained D.O. $\geq$40% by the following sequence: (i) increase vessel pressure to 11 psi, (ii) increase agitation from 156 to 175 cm/see impeller tip speed, and (iii) increase aeration to 0.5 vvm. Foaming is controlled by addition of antifoam Dow 1520-US, as needed.

(Approximately 0.1 ml/L of the antifoam should be added to the medium prior to sterilization to help prevent foaming.) After inoculation, the culture is maintained at pH ≧5.5 with 8N NaOH.

Within 12 hours after pH rises above 6.0, the contents of the seed fermenter are transferred to the main fermenter. The main fermentor medium contains 80 g/L dextrose (ADM)

16 g/L soy flour (ADM nutrisoy)

30 mg/L $FeCl_3 \cdot 6H_2O$ (Sigma/Aldrich)

1.5 mg/L $ZnSO_4 \cdot 7H_2O$ (Sigma/Aldrich)

0.1 mg/L $CuSO_4 \cdot 5H_2O$ (Sigma/Aldrich)

1 mg/L biotin (Sigma/Aldrich)

2 mg/L thiamine. HCl (Sigma/Aldrich)

2 mg/L pantothenic acid (hemicalcium salt) (Sigma/Aldrich). (Adjust to pH 4.8–5.0 pre-sterilization.)

Inoculate main fermentor with Seed fermentor (11.8%). Fermentor temperature is kept at 28° C. Initial agitation is set to 162 cm/sec (ca. 23 rpm), the initial vessel pressure to 6 psi, and the initial aeration rate to 0.15 vmm (ca. 300 scfh).

Oxygen level in the medium is maintained at D.O. ≧40% by i) increasing vessel pressure to 11 psi, ii) increasing agitation to 300 cm/sec impeller tip speed (in increments of ca. 30 cm/sec), and iii) increasing aeration to 0.5 vvm.

pH is profiled according to the following pH control protocol:

Initial pH set to 5.5 post-sterilization. Maintain pH at ≧5.5 with 8N NaOH.

At 24–36 hours after inoculation add the following: 2 g/L $KH_2PO_4$ (110 kg in ca. 700 L $H_2O$).

At 48 hours, if dextrose concentration is ≦60 g/L, change pH setpoint to ≧6.1.

At 72 hours, begin to slowly raise the pH setpoint to ≧6.6 at a rate of ca. 0.1 pH units per hour.

Maintain pH below 7.3 with $H_2SO_4$ addition if necessary.

Fermentor is sampled every 12 hours for biomass and fatty acid analysis, and harvest is begun approximately 3 days after raising pH to ≧6.6 (about 6 days after inoculation). Dry biomass density should be ≧24 g/L. Dextrose concentration in the broth should have dropped from 80 g/L to ≦14 g/L.

Harvest is performed by passing the whole culture broth through a rotary vacuum filter to separate the mycelia from the spend medium.

The results of two typical fermentation runs according to the procedure of this Example are shown in Tables 5 and 6.

TABLE 5

Progress of *M. alpina* Fermentation
Culture mediums = Glucose (80 g/L) +
Soy Flour (16 g/L) + Salts + Vitamins

| log hour | Glucose (g/L) | NH3 (mM) | dry wt. (g/L) | oil content (% of dry wt) | ARA content (% of oil) | Productivity (g oil/L/d) |
|---|---|---|---|---|---|---|
| 0 | 58.0 | | | | | |
| 66 | 43.0 | 12.6 | 14.9% | 33.7% | 0.68 | |
| 94 | 33.0 | 17.0 | 27.0% | 40.0% | 1.17 | |
| 118 | 23.0 | 20.6 | 28.2% | 42.6% | 1.18 | |
| 142 | 16.0 | 17.1 | 39.2% | 44.2% | 1.13 | |
| 165 | 9.6 | 21.5 | 41.5% | 45.5% | 1.30 | |
| 188 | 5.2 | 19.8 | 41.7% | 47.3% | 1.05 | |
| 215 | 1.7 | 23.2 | 46.0% | 48.9% | 1.19 | |
| 237 | 0.2 | 23.1 | 44.8% | 51.2% | 1.05 | |

TABLE 6

Progress of *M. alpina* Fermentation
Culture medium = Glucose (65 g/L) + Soy Flour (16 g/L) +
Salts + Vitamins + Antibiotics

| log hour | Glucose (g/L) | NH3 (mM) | dry wt. (g/L) | oil content (% of dry wt) | ARA content (% of oil) | Productivity (g oil/L/d) |
|---|---|---|---|---|---|---|
| 0 | | | | | | |
| 65 | 36.0 | | 13.0 | 8.2% | 29.0% | 0.39 |
| 90 | 23.0 | | 12.0 | 18.0% | 42.0% | 0.58 |
| 115 | 15.0 | | 14.0 | 30.0% | 47.0% | 0.88 |
| 139 | 9.0 | | 15.0 | 32.0% | 51.0% | 0.83 |
| 171 | 4.0 | | 17.0 | 36.0% | 55.0% | 0.86 |
| 209 | 1.4 | | 12.0 | 36.0% | 57.0% | 0.50 |
| 243 | 0 | | 14 | 37.0% | 60.0% | 0.51 |
| 187 | 0 | | 13 | 34.0% | 64.0% | 0.57 |

I claim:

1. A method for the production of an arachidonic add-containing oil, said oil further comprising no more than one fifth as much eicosapentaenoic acid as arachidonic acid, comprising:

(a) cultivating *Pythium insidiosum* in a culture medium containing a carbon source and a nitrogen source, with air sparging and agitation of the culture medium, to induce said *Pythium insidiosum* to produce an oil containing arachidonic acid and no more than one fifth as much eicosapentaenoic acid as arachidonic acid;

(b) harvesting said *Pythium insidiosum*;

(c) extracting said oil from said harvested *Pythium insidiosum*; and (d) recovering said oil.

2. A method in accordance with claim 1, wherein the oil is essentially free of EPA.

3. A method in accordance with claim 1 or 2, wherein the oil comprises at least 10% ARA.

4. A method in accordance with claim 3, wherein said oil comprises about 30% ARA.

5. A method in accordance with claim 1 or 2, wherein said ARA is in the form of a triglyceride.

6. A method in accordance with claim 1, wherein said oil comprises at least about 10 parts arachidonic acid per part eicosapentaenoic acid.

7. A method in accordance with claim 1, wherein the dissolved oxygen level in the culture medium is maintained at no less than 10% of the air saturation value of the medium throughout the cultivation.

8. A method in accordance with claim 1 wherein the carbon source is initially provided at a concentration of about 10 to about 100 g/L of medium and the nitrogen source is provided at a concentration of from about 2 to about 15 g/L of medium.

9. An oil comprising ARA and no more than one fifth as much EPA as ARA produced by the method of claim 1.

10. An oil in accordance with claim 9 which comprises at least 10% ARA and is essentially free of EPA.

11. An oil in accordance with claim 9 which comprises about 30 % ARA.

12. An oil in accordance with claim 11 which is essentially free of EPA.

13. An oil in accordance with claim 9, wherein ARA is in the form of a triglyceride.

14. A method for the production of an arachidonic acid-containing oil, said oil containing triglycerides wherein at least 25% of the fatty acid residues are ARA, and the amount of EPA residues in the oil is no more than one-fifth the amount of ARA residues, comprising (a) cultivating Mortierella sp. in an aerated fermentor containing culture medium having a carbon source in an amount equivalent to at least 80 g/L glucose and a nitrogen source in an amount equivalent to at least 15 g/L yeast extract;

(b) maintaining the pH between 5 and 6 at the beginning of the cultivation;

(c) maintaining the pH between 7 and 7.5 at the end of the cultivation; and (d) harvesting biomass from the fermentor and recovering said arachidonic acid-containing oil from said biomass.

15. The method of claim 14, wherein the dissolved oxygen level in the culture medium is at least 35 % of the air saturation level.

16. The method of claim 14 or 15 wherein the Mortierella sp. is *M. alpina*.

17. The method according to either claim 1 or claim 14, further wherein crude arachidonic acid-containing oil is recovered from the biomass by extraction with a non-polar solvent and the crude oil is clarified by extraction with a polar organic solvent.

18. The method of claim 17, wherein the non-polar solvent is hexane, and the polar solvent is selected from the group consisting of acetone, ethanol and isopropyl alcohol.

19. A fungal triglyceride oil comprising at least about 30% ARA in the triglyceride and no more than one tenth as much EPA as ARA.

20. A fungal triglyceride oil according to claim 19 comprising at least 30% ARA in the triglyceride and essentially no EPA.

21. The fungal triglyceride oil of claim 19 or 20 wherein the oil contains at least 40% ARA.

22. An oil in accordance with claim 19, or 20, wherein the fungus is Mortierella sp.

23. The oil of claim 22, wherein the fungus is *M. alpina*.

24. A method of providing triglyceride containing ARA to an infant formula which comprises adding a fungal oil comprising at least 30% ARA in the form of triglyceride and comprising no more than one fifth as much EPA as ARA to an infant formula in an amount sufficient to provide an ARA content which corresponds to the amount of ARA in human breast milk.

25. A method in accordance with claim 24, wherein said oil is produced by a species of Mortierella.

26. A method in accordance with claim 25, wherein said oil is produced by *Mortierella alpina*.

27. A method in accordance with claim 24, wherein said oil comprises no more than one tenth as much EPA as ARA.

28. A method in accordance with claim 24, wherein said oil comprises essentially no EPA.

29. Infant formula comprising triglyceride containing ARA in an amount comparable to the amount in human breast milk wherein the ARA is provided by adding to infant formula a sufficient amount of a fungal oil comprising triglyceride containing at least 30% ARA and no more than one fifth as much EPA as ARA.

30. Infant formula in accordance with claim 29, wherein the fungal oil comprises no more than one tenth as much EPA as ARA.

31. Infant formula in accordance with claim 30, wherein said fungal oil is essentially free of EPA.

32. A fungal oil, wherein the oil is from *Pythium insidiosum* and comprises at least about 10% ARA and no more than one tenth as much EPA as ARA.

33. A fungal oil according to claim 32 comprising at least 10% ARA and essentially no EPA.

34. An oil in accordance with claim 32 or 33, wherein ARA is present as a triglyceride.

35. A method of providing ARA to an infant formula which comprises adding a fungal oil from *Pythium insidiosum* comprising at least 10% ARA and comprising no more than one fifth as much EPA as ARA to an infant formula in an amount sufficient to provide an ARA content which corresponds to the amount of ARA in human breast milk.

36. A method in accordance with claim 35, wherein said oil comprises no more than one tenth as much EPA as ARA.

37. A method in accordance with claim 35, wherein said oil comprises essentially no EPA.

38. A method in accordance with claim 35, wherein said oil comprises 30% ARA.

39. Infant formula comprising ARA in an amount comparable to the amount in human breast milk wherein the ARA is provided by adding to infant formula a sufficient amount of a fungal oil from *Pythium insidiosum* comprising at least 10% ARA and no more than one fifth as much EPA as ARA.

40. Infant formula in accordance with claim 39, wherein the fungal oil comprises no more than one tenth as much EPA as ARA.

41. Infant formula in accordance with claim 40, wherein said fungal oil is essentially free of EPA.

42. A method of providing a human with supplemental arachidonic acid (ARA) comprising administering to a human in need of supplemental ARA a composition containing fungal oil containing ARA in the form of triglyceride, said oil containing at least 30% ARA and no more than one fifth as much eicosapentaenoic acid(EPA) as ARA, wherein said oil is present in an amount effective to provide supplemental ARA to said human.

43. The method of claim 42, wherein said composition is administered enterally.

44. The method of claim 42, wherein said composition is administered parenterally.

45. The method of claim 42, wherein said composition is administered topically.

46. The method of claim 42, wherein said human is a pregnant or nursing woman.

47. A cosmetic composition comprising fungal oil containing ARA in the form of triglyceride, said oil containing at least 30% ARA and no more than one fifth as much eicosapentaenoic acid (EPA) as ARA, wherein said oil is present in said composition in an amount effective to assist in maintaining skin tone when said composition is applied topically.

48. The oil in accordance with claim 21, wherein the fungus is Mortierella sp.

49. The oil in accordance with claim 21, wherein the fungus is *M. alpina*.

50. The fungal oil of claim 21, wherein the oil contains at least 50% ARA.

51. The oil in accordance with claim 50, wherein the fungus is Mortierella sp.

52. The oil in accordance with claim 50, wherein the fungus is *M. alpina*.

\* \* \* \* \*

(12) EX PARTE REEXAMINATION CERTIFICATE (7511th)
United States Patent
Kyle

(10) Number: US 5,658,767 C1
(45) Certificate Issued: May 18, 2010

(54) ARACHIDONIC ACID AND METHODS FOR THE PRODUCTION AND USE THEREOF

(75) Inventor: David J. Kyle, Catonsville, MD (US)

(73) Assignee: Martek Biosciences Corporation, Columbia, MD (US)

Reexamination Request:
No. 90/009,107, Apr. 14, 2008

Reexamination Certificate for:
Patent No.: 5,658,767
Issued: Aug. 19, 1997
Appl. No.: 08/367,881
Filed: Jan. 3, 1995

Related U.S. Application Data

(63) Continuation-in-part of application No. 08/202,878, filed on Feb. 28, 1994, now abandoned, which is a continuation of application No. 08/065,507, filed on May 24, 1993, now abandoned, which is a continuation of application No. 07/645,454, filed on Jan. 24, 1991, now abandoned.

(51) Int. Cl.
| | |
|---|---|
| A23C 11/00 | (2006.01) |
| A23C 11/04 | (2006.01) |
| A23L 1/30 | (2006.01) |
| A23L 1/29 | (2006.01) |
| A61K 8/92 | (2006.01) |
| A61K 31/232 | (2006.01) |
| A61K 31/185 | (2006.01) |
| A61K 31/202 | (2006.01) |
| A61K 31/21 | (2006.01) |
| A23D 9/00 | (2006.01) |
| A61Q 19/00 | (2006.01) |
| C12P 7/64 | (2006.01) |
| C11B 1/10 | (2006.01) |
| C11B 1/00 | (2006.01) |

(52) U.S. Cl. ............... 435/134; 426/585; 514/558; 514/560

(58) Field of Classification Search ........... None
See application file for complete search history.

(56) References Cited

U.S. PATENT DOCUMENTS

| | | | |
|---|---|---|---|
| 2,611,706 A | 9/1952 | Bernhart et al. |
| 2,923,628 A | 2/1960 | Otto |
| 3,458,625 A | 7/1969 | Ensor et al. |
| 3,542,560 A | 11/1970 | Tomarelli et al. |
| 3,649,295 A | 3/1972 | Bernhart et al. |
| 4,058,594 A | 11/1977 | Williams |
| 4,216,236 A | 8/1980 | Mueller et al. |
| 4,282,265 A | 8/1981 | Theuer |
| 4,303,692 A | 12/1981 | Gaull |
| 4,513,008 A | 4/1985 | Revici et al. |
| 4,526,793 A | 7/1985 | Ingenbleek et al. |
| 4,526,902 A | 7/1985 | Rubin |
| 4,544,559 A | 10/1985 | Gil et al. |
| 4,614,663 A | 9/1986 | Rule |
| 4,670,285 A | 6/1987 | Clandinin et al. |
| 4,681,896 A | 7/1987 | Horrobin |
| 4,703,060 A | 10/1987 | Traitler et al. |
| 4,752,618 A | 6/1988 | Mascioli et al. |
| 4,780,456 A | 10/1988 | Pistolesi |
| 4,792,418 A | 12/1988 | Rubin |
| 4,810,497 A | 3/1989 | Horrobin |
| 4,820,731 A | 4/1989 | Mascioli et al. |
| 4,826,877 A | 5/1989 | Stewart et al. |
| 4,843,095 A | 6/1989 | Rubin |
| 4,851,343 A | 7/1989 | Herbert et al. |
| 4,868,001 A | 9/1989 | Maruta |
| 4,874,603 A | 10/1989 | Fratzer |
| 4,874,629 A | 10/1989 | Chang et al. |
| 4,876,107 A | 10/1989 | King et al. |
| 4,911,944 A | 3/1990 | Holub |
| 4,920,098 A | 4/1990 | Cotter et al. |
| 4,938,984 A | 7/1990 | Traitler et al. |
| 4,960,795 A | 10/1990 | Salte et al. |
| 4,963,385 A | 10/1990 | Antrim et al. |
| 5,013,569 A | 5/1991 | Rubin |
| 5,116,871 A | 5/1992 | Horrobin |
| 5,120,760 A | 6/1992 | Horrobin |
| 5,130,242 A | 7/1992 | Barclay |
| 5,198,468 A | 3/1993 | Horrobin |
| 5,204,250 A | 4/1993 | Shinmen et al. |
| 5,234,702 A | 8/1993 | Katz et al. |
| 5,338,673 A | 8/1994 | Thepenier et al. |
| 5,374,657 A | 12/1994 | Kyle |
| 5,397,591 A | 3/1995 | Kyle et al. |
| 5,407,957 A | 4/1995 | Kyle et al. |
| 5,550,156 A | 8/1996 | Kyle |
| 5,583,019 A | 12/1996 | Barclay |
| 6,448,055 B1 | 9/2002 | Shimizu et al. |
| 6,746,857 B2 | 6/2004 | Higashiyama et al. |

FOREIGN PATENT DOCUMENTS

| | | |
|---|---|---|
| DE | 3603000 | 8/1987 |
| DE | 3920679 | 1/1991 |
| EP | 0092085 | 3/1986 |
| EP | 0223960 | 6/1987 |
| EP | 0231904 | 8/1987 |
| EP | 0269351 | 6/1988 |
| EP | 0276541 | 8/1988 |
| EP | 0276982 | 8/1988 |
| EP | 0296751 | 12/1988 |
| EP | 332423 | 9/1989 |
| EP | 0404058 | 12/1990 |
| EP | 0404058 | 12/1994 |

(Continued)

OTHER PUBLICATIONS

Bajpai et al., "Effects of Aging Mortierella Mycelium on Production of Arachidonic and Eicosapentaenoic Acids", JOACS, vol. 68, pp. 775–780, Oct. 1991.

(Continued)

*Primary Examiner*—Evelyn Huang

(57) ABSTRACT

The present invention relates to processes for the production of arachidonic acid containing oils, which preferably are substantially free of eicosapentaneoic acid. The invention also relates to compositions containing such oils, in an unmodified form, and to uses of such oils. In a preferred embodiment, *Pythium insidiosum* is cultivated, harvested and the oil is extracted, recovered, and used as an additive for infant formula. In an alternative embodiment, *Mortierella alpina* is cultivated, harvested and the oil is extracted, recovered, and used as an additive for infant formula.

FOREIGN PATENT DOCUMENTS

| | | |
|---|---|---|
| EP | 0957173 | 11/1999 |
| EP | 1642983 | 4/2006 |
| GB | 1446431 | 8/1976 |
| JP | 62/79732 | 4/1987 |
| JP | 63 90598 | 4/1988 |
| JP | 01/038007 | 2/1989 |
| JP | 63-042925 | 2/1989 |
| JP | 01/080250 | 3/1989 |
| JP | 01/132371 | 5/1989 |
| JP | 196255 | 8/1989 |
| JP | 01/196255 | 8/1989 |
| JP | 01/215245 | 8/1989 |
| JP | 01/304892 | 12/1989 |
| JP | 02/257835 | 10/1990 |
| JP | 6 153970 | 6/1994 |
| JP | 10-512444 | 12/1998 |
| WO | WO 89/00606 | 1/1989 |
| WO | WO 90/04391 | 5/1990 |
| WO | WO 90/13656 | 11/1990 |
| WO | WO 91/07498 | 5/1991 |

OTHER PUBLICATIONS

Bajpai et al., "Production of Arachidonic Acid by Mortierella Alpina ATCC 32222", Journal of Industrial Microbiology, vol. 8, pp. 179–186, Jan. 1991.

Lindberg, "Effect of temperature and glucose Supply on the Production of Polyunsaturated Fatty Acids by Fungus Mortierella Alpina CBS 343.66 in Fermentor Cultures", Applied Microbiology and Biotechnology, vol. 39, p. 450–455, (1993).

Totani, "A Simple method for Production of Arachidonic Acid by Mortierella Alpina", Applied Microbiology and Biotechnology, vol. 28, pp. 135–137, (1988).

Yamada et al., "Production of Arachidonic Acidby Mortierella Elongata 1S–5", Agricultural Biology and Chemistry, vol. 51, pp. 785–790, Aug. 1987.

Zhu, "An Inexpensive Medium for Production of Arachidonic Acid by Mortierella Alpina", Journal of Industrial Microbiology and Biotechnology, vol. 30, pp. 75–79, (2003).

Exhibit CAP–13 to Panker Declaration: Boswell et al., 1996, "Preclinical Evaluation of Single–cell Oils that are Highly Enriched with Arachidonic Acid and Docosahexaenoic Acid," Food Chem. Toxicol., 34(7):585–593; and accompanying notarization page regarding Exhibit CAP–13.

Bajpai et al., "Arachidonic Acid Production by Microorganism," Biotechnol. Appl. Biochem., 15:1–10.

Certik et al., 2000, "Kinetic analysis of oil biosynthesis by an arachidoinic acid–producing fungus, Mortierella alpina 1S–4," Appl. Microbiol. Biotechnol. 54:224–230.

Chang et al., 1994, "Production of Arachidonic Acid by Mortierella alpina," J Chin Agr Chem Soc, 32(4):395–405—(English Abstract only).

Chiou et al., 2000, "Characterization of Arachidonic Acid–Producing Fungi Mortierella alpinaK14–25 and Mortierella sp. L9–22, and Optimization of Arachidonic Acid Production," Food Sci Agr Chem, 2(4):202–211.

Eroshin et al., 2000, "Arachidonic acid production by Mortierella alpina with growth–coupled lipid synthesis," Process Biochem., 35:1171–1175.

Higashiyama et al., 1998, "Effect of Mineral Addition on the Growth Morphology of and Arachidonic Acid Production by Mortierella alpina 1S–4," JAOCS, 75(12):1815–1819.

Higashiyama et al., 1999, "Dielectric Analysis for Estimation of Oil Content in the Mycelia of Mortierella alpina," Biotechnol. Bioeng. 65(5):537–541.

Higashiyama et al., 2002, "Production of Arachidonic Acid by Mortierella Fungi," Biotechnol. Bioprocess Eng. 7:252–262.

Hwang et al., 2005, "High–level production of arachidonic acid by fed–batch culture of Mortierella alpina using $NH_4OH$ as a nitrogen source and pH control," Biotechnol. Lett, 27:731–735.

Jang et al., 2005, "Effect of culture media and conditions on polyunsaturated fatty acids production by Mortierella alpina," Bioresour. Technol., 96:1633–1644.

Jin et al., 2008, "A novel two–step fermentation process for improved arachidonic acid production by Mortierella alpina,"0 Biotechnol. Lett, 30:1087–1091.

Koike et al., 2001, "Effect of Consumed Carbon to Nitrogen Ratio on Mycelial Morphology and Arachidonic Acid Production in Cultures of Mortierella alpina," J. Biosci. Bioeng., 91(4):382–389.

Kotula et al., 1995, "Improvements in Procedures for the Production of Eicosapentaenoic Acid by Mortierella," J. Food Qual. 19(4):279–293.

Park et al., 2002, "Monitoring of morphological development of the arachidonic–acid–producing filamentous microorganism Mortierella alpina," Appl. Microbiol. Biotechnol., 59:706–712.

Sajbidor et al., 1990, "Arachidonic Acid Production By Mortierella Sp. S–17 Influence of C/N Ratio," Biotechnol. Lett, 12(6):455–456.

Sajbidor et al., 1993, "Influence of Carbon and Nitrogen Sources on the Lipid Accumulation and Arachidonic Acid Production by Mortierella alpina," Acta Biotechnol., 13(2):185–191.

Singh et al., 1997, "Production of high yields of arachidonic acid in a fed–batch system by Mortierella alpina ATCC 32222," Appl. Microbiol. Biotechnol., 48:1–5.

Zhu et al., 2006, "Optimization of arachidonic acid production by fed–batch culture of Mortierella alpina based on dynamic analysis," Enzyme Microb. Technol., 38:735–740.

Park et al., 2006, "Analysis of Morphological Relationship Between Micro– and Macromorphology of Mortierella Species Using a Flow–Through Chamber Coupled with Image Analysis," J. Eukaryot. Microbiol., 53(3):199–203.

Streekstra, 2005, "Single Cell Oils," "Chapter 5: Arachidonic Acid: Fermentative Production by Mortierella Fungi" (Cohen and Ratledge eds., AOCS Press).

Totani, et al., 1992, "Industrial Applications of Single Cell Oils," Chapter 4: Industrial Production of Arachidonic Acid by Mortierella (Kyle and Ratledge eds., AOCS).

Totani, et al., 2002, "The Role of Morphology during Growth of Mortierella alpina in Arachidonic Acid Production," J. Oleo Science, 51(8):531–538.

Park et al., 1999, "Effect of Nitrogen Source on Mycelial Morphology and Arachidonic Acid Production in Cultures of Mortierella alpina," J. Biosci. Bioeng., 88(1):61–67.

Third Office Action issued in Application No. 200510071295.2, by the Patent Office of the State Intellectual Property Office of the People's Republic of China, Date of Dispatch: Mar. 27, 2009.

European Patent Office Opposition Division Decision on Oct. 3, 2000 in connection with European Patent No. 0 515 460.

European Patent Office Opposition Division: Minutes of the Oral Proceeding on Oct. 12, 2000 in connection with European Patent No. 0 515 460.

European Patent Office Opposition Division Interlocutory Decision in Opposition on Sep. 5, 2005 in connection with European Patent No. 0 515 460.

European Patent Office Opposition Division: Minutes of the Oral Proceeding on Sep. 5, 2005 in connection with European Patent No. 0 515 460.

Birch, et al., 1998, "Visual acuity and the essentiality of docosahexaenoic acid and arachidonic acid in the diet of term infants," *Pediatr. Res.*, 44:201–209; (1998).

Carlson, et al., Inform Abstract (1990).

Clandinin, et al., "Requirements of Newborn Infants for Long Chain Polyunsaturated Fatty Acids", Acta. Paediatr. Scand. Suppl., 351:63–71 (1989).

Clandinin, et al., 2005, "Growth and development of pre–term infants fed infant formulas Containing docosahexaenoic acid and arachidonic acid," *J. Pediatr.*, 146:461–468.

Harris, et al. (*Am. J. Clin. Nutr.* 1984;40:780–85).

Innis, "Essential Fatty Acids in Growth and Development", Prog. Lipid Res., 30(1):39–103 (1991).

Jensen, Textbook Gastroenterol. Nutr. in Infancy, 1989, Chap. 17 (89b)).

O'Connor, et al., 2001, "Growth and development of pre–term infants fed long–chain polyunaturated fatty acids: a prospective, randomized controlled trial," *Pediatr.*, 108:359–371.

Aaronson, et al. Microalgae as a Source of Chemicals and natural Products, Algae Biomass, 1980, pp. 575–601, Shelef, et al. eds., Elsevier/North–Holland Biomedical Press.

Ackman, Problems in Fish Oils and Concentrates, Fats for the Future, 1989, Chp. 13, pp. 189–200, Combie ed.

Agency Response Letter GRAS Notice No. GRN 00109 (Annex C to D49).

Ahern, Tim J.; Katoh, Shigeo and Eizo Sada. *Arachidonic Acid Production by the Red Alga Porphyridium cruentum*, Biotechnology and Bioengineering, 1983, 25:1057–1070.

AKU Strain List, 1990, p. 27.

Algae and Seawee. Rodophyta (Red Algae) & Phaeophyta (Brown Algae) "Seaweed Site" 'http://seaweed.ucg.ie' © 1995–2003 Michael D. Guiry/Seaweed Home Page/Last modified Jan. 22, 2003.

Alternative Medicine, Excerpt from www.usadrug.com, (article can supplement the excerpt).

Amano et al., Chemotaxonomic Significance of Fatty Acid Composition in th eGenus Mortierella (Zygomycetes, Mortierellaceae), Mycotaxon, 1992, 94:257–265.

ANZFA Draft Assessment of Application A428 (Annex A to D49).

Ask Dr. Sears website (2006).

ATCC Letter, Jul. 13, 2004, 1 pg.

ATCC Catalog of Filamentous Fungi, 18$^{th}$ Ed., 1991, pp. 244–246, Jong et al. eds.

Bajpai, et al., Eicosapentaenoic Acid (EPA) Production by *Mortierella alpina* ATCC 32222, Appl. Biochem. Biotech., 1991, 31:267–272.

Beach, et al. Environmental Influences on the Docosahexaenoate Content of the Triacylglycerols and Phosphatidylcholine of a Heterotrophic, Marine Dinoflagellate, *Crypthecodinium cohnii*, Biochim. Biophys. Acta, 1973, 316:56–65.

Behrens, et al. Eicosapentaenoic Acid from Microalgae, Novel Microbial Products for Medicine and Agriculture, 1989, Chp. 28, pp. 253–259, Demain, et al. eds., Soc. for Industrial Microbiology.

Ben–Amotz, Chemical Profile of Selected Species of Microalgae with Emphasis on Lipids, J. Phycol. 1985, 21:72–81.

Bingham, Report on Analysis of Maeli Absolute Powdered Infant formula, Nov. 26, 2004, 8 pgs.

Biochemical Dictionary, Tokyo Biochemical Coterie, 1$^{st}$ Edition, 7$^{th}$ Printing (published Apr. 1, 1987).

Birch et al., Visual Acuity and the Essentiality of Docosahexaenoic Acid and Arachidonic Acid in the Diet in Term Infants, Pediatr. Res., 1998, 44(2):201–209.

Birch et al., A Randomized Controlled Trial of Long–Chain Polyunsaturated Fatty Acid Supplementation of Formula in Term Infants After Weaning at 6 wk of Age, Am. J. Clin. Nutr., 2002, 75–570–580.

Birch et al., Visual maturation of term infants fed long–chain polyunsaturated fatty acid–supplemented or control formula for 12 mo, Am. J. Clin. Nutr., 2005, 81: 871–879.

Bitman, et al. Comparison of the Lipid Composition of Breast Milk from Mothers of Term and Preterm Infants, Am. J. Clin. Nutr., 1983, 38:300–312.

Bjerve, et al. Omega–3 Fatty Acids: Essential Fatty Acids with Important Biological Effects and Serum Phospholipid Fatty Acids as Markers of Dietary ω3–Fatty Acid Intake, Am. J. Clin. Nutri., 1993, 57 (Suppl):801S–806S.

Blacks Medical Dictionary, 1992, 37$^{th}$ Ed., p. 375, Macpherson ed., A&C Black, London.

Borowitzka, Fats, Oils and Hydrocarbons, Microalgae Biotech., 1988, Chp. 10, pp. 257–287, Borowitzka et al. eds., Cambridge Univ. Press.

Bourre, et al. ΔDesaturase in Brain and Liver During Development and Aging, Lipids, 1990, 25:354–356.

Boustani, et al. Enteral Absorption in Man of Eicosapentaenoic Acid in Different Chemical Forms, Lipids, 1987, 22:711–714.

Bracco, et al. Human Milk Lipids and Problems Related to Their Replacement, Extract from Annales Nestle, 1978, 40:55–81.

Carlson et al., Arachidonic acid status correlates with first year growth in preterm infants, Proc. Natl. Acad. Sci. USA, 1993, 90:1073–1077.

Carlson et al., Docosahexaenoic acid status of preterm infants at birth and following feeding with human milk or formula, Am. J. Clin. Nutr., 1986, 44:798–804.

Carlson, et al. Growth and Development of Very Low–Birthweight Infants in Relation to n–3 and n–6 Essential Fatty Acid Status, Essential Fatty Acids and Eicosenoids–Invited Papers form the Third International Congress, 1992, 1:192–196, Sinclair, et al. eds., American Oil Chem. Soc., Champaign, IL.

Carlson, et al. Long Term Docosahexaenoate (DHA) and Ecosapentaenoate (EPA) Supplementation of Preterm Infants: Effects on Biochemistry, Visual Acuity, Information Processing and Growth In Infancy, Inform, Apr. 1990, 1(4):306.

Carlson, Effect of Fish Oil Supplementation on the n–3 Fatty Acid Content of Red Blood Cell Membranes in Preterm Infants, Pediatri. Res., 1987, 21:507–510.

Carlson, Effect of Fish Oil Supplementation on the n–3 Fatty Acid Content of Red Blood Cell Membranes in Preterm Infants, Chem. Abst., 1987, 107:57830c.

Carlson et al., Visual–acuity development in healthy preterm infants: effect of marine–oil supplementation, Am J Clin Nutr 1993, 58:35–42.

Carlson et al., Effect of long–chain n–3 fatty acid supplementation on visual acuity and growth of preterm infants with and without bronchopulmonary dysplasia, Am. J. Clin. Nutr., 1996, 63:687–697.

Clandinin, et al. Long Chain Polyenoic Essential Fatty Acids in Human Milk: Are They of Benefit to the Newborn?, Composition and Physiological Properties of Human Milk, 1985, Schaub J. ed., Elsevier Science.

Clandinin et al., Growth and Development of Preterm Infants Fed Infant formulas Containing Docosahexaenoic Acid and Arachidonic Acid, J. Pediatr., Apr. 2005, pp. 461–468.

Cohen, Production of Eicosapentaenoic and Arachidonic Acids by the Red Alga *Porphyridium Cruentum*, World Conference on Biotechnology for the Fats and Oils Industry, 1988, pp. 285–287, Applewhite, Thomas H. editor.

Cohen et al., The Effect of Temperature on Cell Concentration on the Fatty Acid Composition of Outdoor Cultures of *Porphyridium Cruentum*, Algal Biotechnology, pp. 421–429, T. Stadler et al. eds.

Davies, Yeast Oil From Cheese Whey—Process Development, Single Cell Oil, 1988, Chp. 4, pp. 99–145, Moreton ed., Longman Scientific & Technical/John Wiley & Sons, Inc. New York.

Food Standards Australia New Zealand, DHASCO and ARASCO Oils as Sources of Long–Chain polyunsaturated Fatty Acids in Infant Formula, A Safety Assessment, Jun. 2003, pp. 1–54 (with KR language abstract).

Dupont, Lipids, Present Knowledge in Nutrition, 1990, Chp. 7, pp. 56–66, Intl. Life Sci. Institute Nutrition Foundation, Washington, DC.

Effects of ω–3 Fatty Acid Supplemented Formula on the ω–3 and ω–6 Fatty Acid Content of Red Blood Cell Membrane in Low Birth Weight Infants, J. Japan Pediatrics Soc., 1990, 94(2):224–234.

Garg et al., Effect of Dietary Cholestrerol and/or ω3 Fatty Acids on Lipid Composition and $\Delta^5$–Desaturase Activity of Rat Liver Mocrosomes, J. Nutr., 1988, 118:661–668.

Gibson, A Lack of Correlation Between Linoleate and Arachidonate in Human Breast Milk, Communications, 1984, 19:469–471.

Giovannini, et al. N–3 Supplementation in Atopic Eczema of Children, Health Effects of Fish and Oils, 1989, p. 591, Chandra ed., ARTS Biomedical Publishers and Distributors, St. John's Newfoundland.

Göbbert et al., Abstracts for Poster Presentation: P–1 Microbial Transesterification of Sugar Corynomycolates, J. Am. Oil Chem. Soc., Sep. 1987, 64(9):1261–1262.

Hansson, et al. Effect of Culture Conditions on Mycelial Growth and Production of γ–Linolenic Acid by the Fungus *Mortiererlla ramanniana*, Appl. Microbiol. Biotechnol., 1988. 28:240–246.

Harel et al., Advanced DHA, EPA and ArA enrichment materials for marine aquaculture using single cell heterotrophs, Aquaculture, 2002, 213:347–362. (Annex B to D49).

Harrington, et al., The Polyunsaturated Fatty Acids of Marine Dinoflagellates, J. Protozool, 1970, 17(2):213–219.

Harris et al., Will dietary ω–3 fatty acids change the composition of human milk?, Am. J. Clin. Nutr. 1984, 40:780–785.

Harzer, et al. Changing Patterns of Human Milk Lipids in the Course of the Lactation and During the Day, Am. J. Clin. Nutr., 1983, 37:612–621.

Haskins et al., Steroids and the Stimulation of Sexual Reproduction of a Species of Pythium, CA J. Microbio., Dec. 24, 1964, 10:187–195.

Haug, Capillary Gas Chromatography of Fatty Acid Methyl Esters from Human Mile Lipid Subclasses, J. of Chromatoghrphy, 1983, 279:549–553.

Heird, Biological Effects and Safety Issues Related to Long–Chain Polyunsaturated Fatty Acids in Infants, Lipids, 1999, 34(2):207–213.

Henderson, et al. Lipid Composition and Biosynthesis in the Marine Dinoflagellate *Crypthecodinium cohnii*, Phytochem., 1988. 27:1679–1683.

Hoffman et al., Impact of Early Dietary Intake and Blood Lipid Composition of Long–Chain Polyunsaturated Fatty Acids on Later Visual Development, J. Pediatr. Gastroenterol. Nutr., Nov. 2000, 31(5)540–553.

Hoffman et al., Visual Function in Breast–Fed Term Infants Weaned to Formula With or Without Long–Chain Polyunsaturates at 4 to 6 Months: A Randomized Clinical Trial, J. Pediatr. 2003, 142: 669–677.

Holman, Nutritional and metabolic interrelationships between fatty acids, Federation Proceedings, 1964, 23:1062–1067.

Hori et al., Composition Analysis of Fats and oils Comprising of Polyunsaturated Fatty Acids by HPLC/FAB–MS II, Yukagaku, 1993, 42:989–955.

Ikeda et al., Digestion and lymphatic transport of eicosapentaenoic and docosahexaenoic acids given in the form of triacylglycerol, free acid and ethyl ester in rates, Biochim. Biophys. Acta, 1995, 1259:297–304.

Innis, et al. Plasma and Red Blood Cell Fatty Acids of Low–Birth–Weight Infants Fed Their mother's Expressed Breast Milk of Preterm–Infant Formula, Am. J. Clin. Nutr., 1990, 51:994–1000.

Innis et al., Docosahexaenoic acid and arachidonic acid enhance growth with no adverse effects in preterm infants fed formula, J. of Pediatr., May 2002, 140:547–554.

Ito, et al. Health Food Microcapsules Containing Unsaturated Fatty Acids for the Control of Cholesterol in Blood, Chem. Abst., 1985, 104:4865z.

Jensen, The Lipids in Human Milk, 1989, pp. 192–200, CRC Press, Boca Raton, FL.

Jensen, The Lipids in Human Milk, Prog. Lipid Res., 1996, 35(1):53–92.

Jensen et al., Lipids in Human Milk–Composition and Fat Soluble Vitamins, Textbook of Gastroenterology and Nutrition in Infancy, $2^{nd}$ Ed., 1989, Chp. 17, pp. 157–208, Lebenthal ed., Raven Press, Ltd., NY.

Johns et al., Fatty acid composition of ten marine algae from Australian waters, Phytochemistry, 1979, 18:799–802.

Karne, et al., Use of Fish Oil Fatty Acids (EPA and DHA) in Nutrition–Supplementing Foods and in Drugs, Chem. Abst., 1984, 100:66638d.

Kneebone et al., Fatty acid composition of breast milk from three racial groups from Penang, Malaysis, Am. J. Clin. Nutr., 1985, 41:765–769.

Kolestzko, Abstract from 3d Int. Congress on Polyunsaturated Fatty Acids in Adelaide, AU, 1992.

Koletzko, Effects of dietary long–chain polyunsaturated fatty acids on the essential fatty acids status of premature infants, Eur. J. Pediatr., 1989, 148:669–675, Koletzko et al., Arachidonic Acid and Early Human Growth: Is there a Relation?, Ann. Nutr. Metab., 1991, 35:128–131.

Koletzko et al., Report of Workshop: Long chain polyunsaturated fatty acids (LC–PUFA) and perinatal development, Acta Paediatr, 2001, 90 :460–464.

Krokan et al., The enteral bioavailability of eioscapentaenoic acid and docosahexaenoic acid is a good from ethyl esters and from glyceryl esters in spite of lower hydrolytic rates by pancreatic lipase in vitro, Biochim. Biophys. Acta, 1993, 1168:59–67.

Kuwahara, Formation of Nicotinic Acid Ribonucleoside by an Enzyme Preparation and Growing Mycelium of *Aspergillus niger*, Agric. Bio. Chem., 1977, 41(4):625–629.

Kyle, Microbial Omega–3–Containing Fats and Oils for Food Use, Adv. Applied Biotech, 1991, 12:167–183.

Kyle, Market Application for Microalgae, JOACS, 1989, 66:648–651.

Kyle, et al., Chapter 16, Bioproduction of Docosahexaenoic Acid (DHA) by Microalgae, Ind. Appl. of Single Cell Oil, 1992, pp. 287–300, American Oil Chemists Society, Illinois.

Letter from the FDA Department of Health and Human Services. To Henry Linsert, Jr. of Martek Biosciences Corporation from Christine J. Lewis, Ph.D. of the Office of Nutritional Product, Labeling and Dietary Supplements and Alan M. Rulis, Ph.D. of the Office of Premarket Approval dated Mar. 1, 2001.

Liu, et al. Increase in Plasma Phospholipid Docosahexaenoic and Eicosapentaenoic Acids as a Reflection of Their Intake and Mode of Administration, Pedatr. Res., 1987, 22:292–296.

Liu et al., In vitro hydrolysis of fungal oils: Distribution of Arachidonic Acid–containing Triacylglycerol molecular species, JAOCS, 75, 4 (1998) 507–510.

List of Cultures, 1988, 8$^{th}$ Ed. vol. 1. Institute of Fermentation, Osaka.

Lösel, Fungal Lipids, Microbial Lipids, 1988, vol. 1, Chapter 10, pp. 699–806.

Martek Biosciences Corporation, Life's DHA, Internet Resource (healthcare.martek.com), Feb. 22, 2008, 1 pg.

Moreton, Physiology of Lipid Accumulating Yeasts, Single Cell Oil, 1988, Chp. 1, pp. 1–11, Moreton ed., Longman Scientific & Technical/John Wiley & Sons, Inc. New York.

Morrison et al., Fatty Acid Composition of Milk Phospholipids II Sheep, Indian buffalo and Human Milk, Lipids, 1996, 2(12):178–182.

Murray et al., Standard Definition of Terms Relating to Mass Spectrometry, 2006, 4 pgs.

Nassar et al., The Influence of Dietary Manipulation with n–3 and n–6 Fatty Acids on Liver and Plasma Phospholipid Fatty Acids in Rats, Lipids, 1986, 21:652–656.

Nettleton, Omega–3 Fatty Acids in Early Human Development, Omega–3 Fatty Acids & Health, 1995, Chp. 6, pp. 249–275, Chapman & Hall, New York.

O'Connor et al., Growth and Development in Preterm infants Fed Long–Chain Polyunsaturated Fatty Acids: A Prospective, Randomized Controlled Trial, Pediatrics, Aug. 2001, 108(2):359–371.

Ohsugi et al., Biosynthesis of Biotin–Vitamers from unsaturated higher Fatty Acids by Bacteria, J. Nutr. Sci. Vitaminol., 1985, 31:253–263.

Olson et al., Arachidonic acid incorporation into lipids of term human amnion, Am. J. Obstet. Gynecol. 1988, 159:995–1001.

Packard, Macronutrients and Energy, Human Milk and Infant Formula, 1982, Chapter 1, pp. 7–49.

Packard, Infant Formula Composition, Formulation and Processing, Human Milk and Infant Formula, 1982, Chapter 6, pp. 140–175.

Pohl, et al., Fatty Acids and Lipids of Marine Algae and the Control of Their Biosynthesis by Environmental Factors, Marine Algae in Pharmaceutical Science, 1979, pp. 473–523, Hoppe, et al. eds., Walter de Grwyler, Berlin–New York.

Puppione, et al., Marine Mammals: Animals Models for Studying the Digestion and Transport of Dietary Fats Enriched in ωFatty Acids. Position Analyses of Milk Fat Triacylglycerol Molecules, Dietary ω–3 and ω–6 Fatty Acids, 1988, pp. 361–365, Galli et al. eds., Plenum Press.

Ratledge, The potential of Microorganisms for Oil Production—A Review of Recent Publication, Proc. World Conf. Emerging Technol. in the Fats Oils Industr., 1986, pp. 318–330 Baldwin ed., Am. Oil Chem Soc.

Ratledge, Lipids, Biotechnology, vol. 4, Chp. 7, pp. 186–196, Pape et al. eds., VCH Weinheim, Germany.

Sanders, et al. Studies of Vegans: The Fatty Acid Composition of Plasma Choline Phosphoglycerides, Erythrocytes, Adipose Tissue, and Breast Milk, and some Indicators of Susceptibility to Ischemic Heart Disease in Vegans and Omnivore Controls, Am. J. Clin. Nutr., 1978, 31:805–813.

Sanders et al., The influence of different types of ω3 polyunsaturated fatty acids on blood lipids and platelet function in healthy volunteers, Clin. Sci., 1983, 64:91–99.

Sawada et al., Effect of Column Temperature on Improvement of Resolution in Separating Triglyceride Molecular Species Containing highly Unsaturated Fatty Acids by Reverse Phase High Performance Liquid Chromatograpy, Nippon Suisan Gakkaishi, 1992, 58(7):1313–1317.

Schrijver et al., Effects of Dietary Long–Chain Fatty Acids on the Biosynthesis of Unsaturated Fatty Acids in the Rat, J. Nutr., 1982, 112: 619–626.

Shifrin, et al. Plytoplankton Lipids: Environmental Influences on Production and Possible Commercial Applications, Algae Biomass, 1980, pp. 627–645 Shelef et al. eds., Elsevier/North–Holland Biomedical Press.

Shifrin, Oils from Microalgae, Biotechnology for the Oils and Fats Industry, 1984, Chp. 14, pp. 145–162, Ratledge et al., eds., Am. Oil Chem. Soc., Champaign, IL.

Shimizu, Microbial Culture Collection of Laboratory of Applied Microbiology Kyoto University, May 1992, 1 pg.

Shimizu, et al. Production of Eicosapentaenoic Acid by Mortierella Fungi, J. Am. Oil Chem. Soc., 1988, 65(9):1455–1459.

Shimizu, et al. Production of C–20 Polyunsaturated Fatty Acids by Fungi, ISF–JOCS World Conference, 1988, 7 pgs.

Shimizu et al., Occurrence of a Novel Sterol, 24,25–Methylenecholest–5–en–3β–ol in *Mortierella alpina* 1S–4, Lipids, 1992, 27(6):481–483.

Shimizu, et al. Conversion of Linseed Oil to an Eicosapentaenoic Acid–Containing Oil by *Mortierella alpina* 1S–4 at Low Temperature, Appl. Microb. Biotechnol., 1989, 32:1–4.

Shimizu et al., Fungal Mycelia As A Novel Source of Eicosapentaenoic Acid: Activation of Enzyme(s) Involved in Eicosapentaenoic Acid Production at Low Temperature, Biochemical and Biophysical Research Communications, 1988, 150(1):335–341.

Shimizu et al., Microbial Production of Polyunsaturated Fatty Acids (Vitamin–F Group), Biotechnology of Vitamins, Pigments and Growth Factors, 1989, Chp. 7, pp. 106–121, Vandamme ed., Elsevier.

Shimizu et al., Production of Dietary and pharmacologically Important Polyunsaturated Fatty Acids by Microbiological Processes, Comments Agric. & Food Chem., 1990, 2(3):211–235.

Shinmen, et al. Production of Arachidonic Acid by *Mortierella* fungi: Selection of a Potent Producer and Optimization of Culture Conditions for Large–Scale Production, Appl. Microb. Biotech., 1989, 331:11–16.

Similac, Formula Compositions of Infant Formula Products Marketed in Korea, 4 pgs. (Internet site www.similac.co.kr/abbott/world/world1_1.jsp).

Simopoules, Omega 3 Fatty Acids, Health and Disease, 1990, p. 136, Lees et al. eds.

Simopoulos et al., Workshop on the Essentiality of and Recommended Dietary Intakes of Omega–6 and Omega–3 Fatty Acids, ISSFAL Newsletter, 6(2):14–16, J. of Lipid Nutr., 1999, 8(2):128–135.

Simopoulos et al., Workshop on the Essentiality of and Recommended Dietary Intakes of Omega–6 and Omega–3 Fatty Acids, J. Am. Coll. Nutr., 1999, 18(5):487–489.

Smith et al., Chemical marker for the differentiation of Group A and Group B Streptococci by Pyrolysis–Gas Chromatography–mass spectrometry, Anal. Chem., 1987, 59:1410–1413.

Sonnenborn, et al. Purification and Properties of the Fatty Acid Synthetase Complex from the Marine Dinoflagellate, *Crypthecodinium cohnii*, Biochem. Biophys. Acta, 1982, 712: 523–534.

Sridhar et al., Incorporation of Eicosapentaenoic and Docosahexaenoic Acids into Groundnut Oil by Lipase–Catalyzed Ester Interchange, JAOCS, Oct. 1992, 69(10):1041–1042.

Suntory, Arachidonic Acid–Containing Oil (SUNTGA 40S), 8 pgs.

Suntory technical presentation, Jul. 11, 2006, 29 pgs.

Suzuki, Lipids of Fungi and Bacteria, Comprehensive Lipid Science, 1989, pp. 767–781, Kayama ed., Koseisha Koseikaku Co., Ltd.

Takashi, et al. Feeds Containing Highly Unsaturated Fatty acids and Vitamin E for swine and production of pork using the feeds, Chem. Abst., 1991, 114: 41472w.

Totani, et al. The Filamentous Fungus *Mortierella alpina*, High in Arachidonic Acid, Lipids, 1987, 22(12):1060–1062.

Totani, et al, Production of Arachidonic Acid by *Mortierella alpina*, ISF–JOCS World Conference, 1988, pp. 993–999.

Totani et al., An Improved Method of Arachidonic Acid Production by *Mortierella alpina*, J. Jpn. Oil. Chem. Soc., 1987, 36:328–331.

Uchida et al., Continuous Production of NADP by Immobilized *Achromobacter aceris* Cells, Biotech. & Bioeng., 1978, 20:255–266.

U.S. Food and Drug Administration Subchapter B—Food for Human Consumption Part 107 Infant Formula (attachment of Patentee to letter of 25.2.05).

Vitamins, J. of the Vitamin Soc. of Japan, 1988, 62(8):439–445.

Volkman, et al. Fatty Acid and lipid Composition of 10 Species of Microalgae Used in Mariculture, J. Esp. Mar. Biol., 1989, 128:219–240.

Weaver, et al. The Effect of Positional Placement of EPA in Ingested Triglyceride on EPA Accumulation in Human Platelet and Plasma Phospholipides, Health Effects of Fish and Fish Oils, 1989, Chp. 39, pp. 581–589, Clandra ed., St. John's Newfoundland.

Weete et al., Fatty Acids and Sterols of Selected Hyphochytriomycetes and Chytridiomycetes, Exp. Mycology, 1989, 13:183–195.

Yahiro, Nutritional Research for improvement of fat blending in infant formula, Research Report No. 90 of Institute of Snow Brand Milk Products Co. Ltd., 1990, 90:137–203.

Yamada, et al. Production of Dihomo–y–linolenic Acid, Arachidonic Acid and Eicosapentaenoic Acid by Filamentous Fungi, Ind. Appl. Single Cell Oils, 1992, Chp. 7, pp. 118–138.

Yamada, et al. Production of Arachidonic Acid and Eicosapentaenoic Acid by Microorganisms, Proc World Congr. Biotechnol. for Oils and Fats Industr., 1987, pp. 173–177, Applewhite, ed., Am. Oil Chem. Soc.

Yamada, et al., Biotechnological Processes for Production of Poly–Unsaturated Fatty Acids, J. Disp. Sci. & Tech., 1989, 10:561–579.

Yamada et al., Polyunsaturated Fatty Acid Produced by Microorganisms, Annual Report, Dai–Ichi Kogyo Seiyaku, Ltd., 1990, No. 466, pp. 2–7, Company Report of First Industrial Pharmaceutical Company (Japan).

Yamada et al., (Korean Language) Polyunsaturated Fatty Acid Produced by Microorganisms, Annual Report, Dai–Ichi Kogyo Seiyaku, Ltd., 1990, No. 466, pp. 2–7, Company Report of First Industrial Pharmaceutical Company (Japan).

Yazawa, Production of Lipid by Microorganism, Resource/Environment and Microorganism—Its new developments, Sagami Chem. Research Center, 1989, 5(6): 66–75.

Yeh, et al. Enrichment of (n–3) Fatty Acids of Suckling Rats by Maternal Dietary Menhaden Oil, Chem. Abstr., 1990, 113:39304d.

Yongmanitchai, et al., Omega–3 Fatty Acids: Alternative Sources of Production, Process Biochem., 1989, 24:117–125.

Yoshifusi, Introduction to the Patent Act, pp. 110–111.

Yoshifusi, Introduction to the Patent Act, pp. 164–165.

Carlson et al., First year growth of preterm infants fed standard compared to marine oil n–3 supplemented formulas, Lipids, 1992, 27(11):901–907.

Clandinin et al., Requirements of newborn infants for long chain polyunsaturated fatty acids, Acta. Paediatr. Scand. Suppl., 1989, 351:63–71.

Codex Alimentarius Commission, Codex Standard for Infant Formula, Stan 72–1981.

Crawford et al., Essential fayy acid requirement in infancy, Am. J. Clin. Nutr. 1978, 31:2181–2185.

Foote et al., Brain synaptosomal, liver, plasma, and red blood cell lipids in piglets fed exclusively on a vegetable–oil–containing formula with and without fish–oil supplements, Am. J. Clin. Nutr., 1990, 51(6):1001–1006.

Hrboticky et al., Effect of linoleic acid–rich infant formula feeding on brain synaptosomal lipid accretion and enzyme thermotropic behavior in the piglet, J. Lipid Res., 1989, 30(8):1173–1184.

Innis, Essential fatty acids in growth and development, Prog. Lipid Res., 1991, 30(1):39–103.

Koletzko et al., Fat content and fatty acid composition of infant formulas, Acta. Paediatr. Scand., 1989, 78:513–521.

Life Sciences Reseach Office (LSRO) Report, Assessment of Nutrient Requirements for Infant Formulas, J. Nutr., 1998, 128(11S):2105S–2106S.

Purvis et al., Fatty acid accretion during perinatal brain growth in the pig. A model for fatty acid accretion in human brain, Comp. Biochem. Physiol., 1982, 72B(2):195–199.

Putnam et al., The effect of variations in dietary fatty acids on the fatty acid composition of erythrocyte phosphatidylcholine and phosphatidylethanolamine in human infants, Am. J. Clin. Nutr., 1982, 36:106–114.

Yuhas et al., Human Milk Fatty Acid Composition from Nine Countries Varies Most in DHA, Lipids, Sep. 2006, 41:851–858.

Jareonkitmongkol et al., Fatty acid desaturation–defective mutants of an arachidonic–acid–producing fungus, *Mortierella alpina* 1S–4, J Gen. Micorbio., 1992, 138:997–1002.

Novel Foods Unit, Arachidonic acid rich oil SUNTGA 40S. Assessment of safety for the consumer, in accordance with European Regulation 258/97 concerning novel foods and novel ingredients, Oct. 19, 2005, pp. 1–55, MEB, The Netherlands.

Burley et al., Egg Yolk: Structure and Properties, The Avian Egg Chemistry and Biology, 1989, Chp. 7, pp. 171–183.

Young, The Chemical & Physical Properties of Crude Fish Oils for Refiners & Hydogenators, Fish Oil Bulletin, Jun. 1986, No. 18, pp. 1–18.

Carlson et al., Am J. Clin. Nutr., 44:798–804 (1986).

Yamada et al., Dispersion Sci. Tech., 10(4&5), 561–579 (1989).

US 5,658,767 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 19–31, 42 and 48–52 are cancelled.

New claims 53–132 are added and determined to be patentable.

Claims 1–18, 32–41 and 43–47 were not reexamined.

*53. A method of providing triglyceride containing ARA to an infant formula which comprises adding a fungal oil comprising at least 30% ARA in the form of triglyceride and comprising no more than one fifth as much EPA as ARA to an infant formula in an amount sufficient to provide an ARA content which corresponds to the amount of ARA in human breast milk, wherein the fungal oil is produced by aerobically culturing Mortierella in a fermentor having a dissolved oxygen level that is maintained at greater than or equal to 40% of air saturation level at least throughout the period of maximum oxygen uptake.*

*54. Infant formula comprising triglyceride containing ARA in an amount comparable to the amount in human breast milk wherein the ARA is provided by adding to infant formula a sufficient amount of a fungal oil comprising triglyceride containing at least 30% ARA and no more than one fifth as much EPA as ARA, wherein the fungal oil is produced by aerobically culturing Mortierella in a fermentor having a dissolved oxygen level that is maintained at greater than or equal to 40% of air saturation level at least throughout the period of maximum oxygen uptake.*

*55. A method of providing a human with supplemental arachidonic acid (ARA) comprising administering to a human in need of supplemental ARA a composition containing fungal oil containing ARA in the form of triglycerid, said oil containing at least 30% ARA and no more than one fifth as much eicosapentaenoic acid (EPA) as ARA, wherein said oil is present in an amount effective to provide supplemental ARA to said human, wherein the fungal oil containing ARA is produced by aerobically culturing Mortierella in a fermentor having a dissolved oxygen level that is maintained at greater than or equal to 40% of air saturation level at least throughout the period of maximum oxygen uptake.*

*56. A method of providing triglyceride containing ARA to an infant formula which comprises: 1.) producing a fungal oil comprising at least 30% ARA in the form of triglyceride and comprising no more than one fifth as much EPA as ARA, by aerobically culturing Mortierella in a fermentor having a dissolved oxygen level that is maintained at greater than or equal to 40% of air saturation level at least throughout the period of maximum oxygen uptake, recovering said oil, and optionally performing an additional purification step on said oil; and 2.) adding a fungal oil produced according to step 1) to an infant formula in an amount sufficient to provide an ARA content which corresponds to the amount of ARA in human breast milk.*

*57. A fungal triglyceride oil comprising at least about 30% ARA in the triglyceride and no more than one tenth as much EPA as ARA, produced by aerobically culturing Mortierella in a fermentor under culture conditions having a dissolved oxygen level that is maintained at greater than or equal to 40% of air saturation level at least throughout the period of maximum oxygen uptake.*

*58. A fungal triglyceride oil comprising at least about 50% ARA in the triglyceride and no more than one tenth as much EPA as ARA, produced by aerobically culturing Moritierella in a fermentor under culture conditions having a dissolved oxygen level that is maintained at greater than or equal to 40% of air saturation level at least throughout the period of maximum oxygen uptake.*

*59. A method in accordance with any one of claims 53, 55, or 56, wherein the Mortierella is Mortierella alpina.*

*60. Infant formula in accordance with claim 54, wherein the Mortierella is Mortierella alpina.*

*61. Fungal oil in accordance with claim 57 or claim 58, wherein the Mortierella is Mortierella alpina.*

*62. A method in accordance with any one of claims 53, 55, or 56, wherein the fungal oil comprises no more than one twentieth as much EPA as ARA.*

*63. Infant formula in accordance with claim 54, wherein the fungal oil comprises no more than one twentieth as much EPA as ARA.*

*64. Fungal oil in accordance with claim 57 or claim 58, wherein the fungal oil comprises no more than one twentieth as much EPA as ARA.*

*65. A method in accordance with any one of claims 53, 55, or 56, wherein the fungal oil comprises essentially no EPA.*

*66. Infant formula in accordance with claim 54, wherein the fungal oil comprises essentially no EPA.*

*67. Fungal oil in accordance with claim 57 or claim 58, wherein the fungal oil comprises essentially no EPA.*

*68. A method in accordance with any one of claims 53, 55, or 56, wherein the fungal oil comprises at least 40% ARA.*

*69. Infant formula in accordance with claim 54, wherein the fungal oil comprises at least 40% ARA.*

*70. Fungal oil in accordance with claim 57, wherein the fungal oil comprises at least 40% ARA.*

*71. A method in accordance with any one of claims 53, 55, or 56, wherein the ARA-containing fungal oil is produced at an average rate of at least 1.0 g/L/day.*

*72. Infant formula in accordance with claim 54, wherein the ARA-containing fungal oil is produced at an average rate of at least 1.0 g/L/day.*

73. Fungal oil in accordance with claim 57 or claim 58, wherein the ARA-containing fungal oil is produced at an average rate of at least 1.0 g/L/day.

74. A method in accordance with any one of claims 53, 55, or 56, wherein the ARA-containing fungal oil is produced at an average rate of at least 2.0 g/L/day.

75. Infant formula in accordance with claim 54, wherein the ARA-containing fungal oil is produced at an average rate of at least 2.0 g/L/day.

76. Fungal oil in accordance with claim 57 or claim 58, wherein the ARA-containing fungal oil is produced at an average rate of at least 2.0 g/L/day.

77. A method in accordance with any one of claims 53, 55, or 56, wherein the Mortierella biomas is harvested after culturing and dried using fluid bed drying or spray drying prior to recovery of the oil.

78. Infant formula in accordance with claim 54, wherein the Mortierella biomass is harvested after culturing and dried using fluid bed drying or spray drying prior to recovery of the oil.

79. Fungal oil in accordance with claim 57 or claim 58, wherein the Mortierella biomass is harvested after culturing and dried using fluid bed drying or spray drying prior to recovery of the oil.

80. A method in accordance with any one of claims 53, 55, or 56, wherein the dissolved oxygen level is maintained at least throughout the growth phase.

81. Infant formula in accordance with claim 54, wherein the dissolved oxygen level is maintained at least throughout the growth phase.

82. Fungal oil in accordance with claim 57 or claim 58, wherein the dissolved oxygen level is maintained at least throughout the growth phase.

83. A method in accordance with any one of claims 53, 55, or 56, wherein the dissolved oxygen level is maintained throughout the fermentation.

84. Infant formula in accordance with claim 54, wherein the dissolved oxygen level is maintained throughout the fermentation.

85. Fungal oil in accordance with claim 57 or claim 58, wherein the dissolved oxygen level is maintained throughout the fermentation.

86. A method of providing triglyceride containing ARA to an infant formula which comprises obtaining a fungal oil produced by culturing Mortierella under fed batch conditions in a high nutrient medium comprising a carbon source in an amount equivalent to at least 75 g/L glucose and a nitrogen source in an amount equivalent to at least 15 g/L yeast extract, wherein the C:N ratio of the culture is equivalent to or greater than a C:N ratio for glucose:yeast extract at 5:1 (w/w), and wherein the dissolved oxygen level of the medium is maintained at a level high enough to relieve growth inhibition by said nutrient medium, said fungal oil comprising at least 30% ARA in the form of triglyceride and comprising no more than one fifth as much EPA as ARA, and adding said fungal oil to an infant formula in an amount sufficient to provide an ARA content which corresponds to the amount of ARA in human breast milk.

87. A method of providing a human with supplemental arachidonic acid (ARA) comprising obtaining a fungal oil produced by culturing Mortierella under fed batch conditions in a high nutrient medium comprising a carbon source in an amount equivalent to at least 75 g/L glucose and a nitrogen source in an amount equivalent to at least 15 g/L yeast extract, wherein the C:N ratio of the culture is equivalent to or greater than a C:N ratio for glucose:yeast extract at 5:1 (w/w), and wherein the dissolved oxygen level of the medium is maintained at a level high enough to relieve growth inhibition by said nutrient medium, said fungal oil containing ARA in the form of triglyceride and containing at least 30% ARA and no more than one fifth as much EPA as ARA, and administering to a human in need of supplemental ARA a composition containing said fungal oil, wherein said fungal oil is present in an amount effective to provide supplemental ARA to said human.

88. The method of any one of claims 86 or 87, wherein the nitrogen source is soy flour.

89. The method of any one of claims 86 or 87, wherein the Mortierella is Mortierella alpina.

90. The method of claim 89, wherein the Mortierella alpina are cultured until a biomass density of at least about 25 g/L dry weight is achieved.

91. The method in accordance with claim 86 or 87, wherein the fungal oil is produced at an average rate of at least 1.0 g/L/day.

92. The method in accordance with claim 86 or 87, wherein the fungal oil is produced at an average rate of at least 2.0 g/L/day.

93. The method in accordance with claim 86 or 87, wherein the fungal oil comprises no more than one tenth as much EPA as ARA.

94. The method in accordance with claim 86 or 87, wherein the fungal oil comprises no more than one twentieth as much EPA as ARA.

95. The method in accordance with claim 86 or 87, wherein the fungal oil comprises essentially no EPA.

96. The method in accordance with claim 86 or 87, wherein the fungal oil comprises at least 40% ARA.

97. The method in accordance with claim 86 or 87, wherein the fungal oil comprises at least 50% ARA.

98. The method in accordance with claim 86 or 87, wherein the Mortierella biomass is harvested after culturing and dried using fluid bed drying or spray drying prior to recovery of the fungal oil.

99. A fungal triglyceride oil comprising at least 50% ARA in the triglyceride and no more than one tenth as much EPA as ARA, wherein said fungal oil is produced by culturing Mortierella under fed batch conditions in a high nutrient medium comprising a carbon source in an amount equivalent to at least 75 g/L glucose and a nitrogen source in an amount equivalent to at least 15 g/L yeast extract, wherein the C:N ratio of the culture is equivalent to or greater than a C:N ratio for glucose:yeast extract at 5:1 (w/w), and wherein the dissolved oxygen level of the medium is maintained at a level high enough to relieve growth inhibition by said high nutrient medium.

100. A fungal triglyceride oil comprising at least 30% ARA in the triglyceride and no more than one tenth as much EPA as ARA, wherein said fungal oil is produced by culturing Mortierella under fed batch conditions in a high nutrient medium comprising a carbon source in an amount equivalent to at least 75 g/L glucose and a nitrogen source in an amount equivalent to at least 15 g/L yeast extract, wherein the C:N ratio of the culture is equivalent to or greater than a C:N ratio for glucose:yeast extract at 5:1 (w/w), and wherein the dissolved oxygen level of the medium is maintained at greater than or equal to 40% of air saturation to relieve growth inhibition by said high nutrient medium.

101. The fungal triglyceride oil according to claim 99 or 100, wherein the nitrogen source is soy flour.

102. The fungal triglyceride oil according to claim 99 or 100, wherein the Mortierella is Mortierella alpina.

103. The fungal triglyceride oil of claim 102, wherein the Mortierella alpina are cultured until a biomass density of at least about 25 g/L dry weight is achieved.

104. The fungal triglyceride oil according to claim 99 or 100, wherein the fungal oil is produced at an average rate of at least 1.0 g/L/day.

105. The fungal triglyceride oil according to claim 99 or 100, wherein the fungal oil is produced at an average rate of at least 2.0 g/L/day.

106 The fungal triglyceride oil according to claim 99 or 100, wherein the fungal oil comprises no more than one twentieth as much EPA as ARA.

107. The fungal triglyceride oil according to claim 99 or 100, wherein the fungal oil comprises essentially no EPA.

108. The fungal triglyceride oil according to claim 100, wherein the fungal oil comprises at least 40% ARA.

109. The fungal triglyceride oil according to claim 100, wherein the fungal oil comprises about 50% ARA.

110. The fungal triglyceride oil according to claim 99 or 100, wherein the Mortierella biomass is harvested after culturing and dried using fluid bed drying or spray drying prior to recovery of the fungal oil.

111. Infant formula comprising triglyceride containing ARA in an amount comparable to the amount of ARA in human breast milk, wherein the ARA is provided by adding to infant formula a sufficient amount of fungal oil comprising triglyceride containing at least 50% ARA and no more than one fifth as much EPA as ARA, wherein said fungal oil is produced by culturing Mortierella under fed batch conditions in a high nutrient medium comprising a carbon source in an amount equivalent to at least 75 g/L glucose and a nitrogen source in an amount equivalent to at least 15 g/L yeast extract, wherein the C:N ratio of the culture is equivalent to or greater than a C:N ratio for glucose:yeast extract at 5:1 (w/w), and wherein the dissolved oxygen level of the medium is maintained at a level high enough to relieve growth inhibition by said high nutrient medium.

112. Infant formula comprising triglyceride containing ARA in an amount comparable to the amount of ARA in human breast milk, wherein the ARA is provided by adding to infant formula a sufficient amount of fungal oil comprising triglyceride containing at least 30% ARA and no more than one fifth as much EPA as ARA, wherein said fungal oil is produced by culturing Mortierella under fed batch conditions in a high nutrient medium comprising a carbon source in an amount equivalent to at least 75 g/L glucose and a nitrogen source in an amount equivalent to at least 15 g/L yeast extract, wherein the C:N ratio of the culture is equivalent to or greater than a C:N ratio for glucose:yeast extract at 5:1 (w/w), and wherein the dissolved oxygen level of the medium is maintained at greater than or equal to 40% of air saturation to relieve growth inhibition by said high nutrient medium.

113. Infant formula according to claim 111 or 112, wherein the nitrogen source is soy flour.

114. Infant formula according to claim 111 or 112, wherein the Mortierella is Mortierella alpina.

115. Infant formula according to claim 114, wherein the Mortierella alpina are cultured until a biomass density of at least about 25 g/L dry weight is achieved.

116. Infant formula according to claim 111 or 112, wherein the fungal oil is produced at an average rate of at least 1.0 g/L/day.

117. Infant formula according to claim 111 or 112, wherein the fungal oil is produced at an average rate of at least 2.0 g/L/day.

118. Infant formula according to claim 111 or 112, wherein the fungal oil comprises no more than one tenth as much EPA as ARA.

119. Infant formula according to claim 111 or 112, wherein the fungal oil comprises no more than one twentieth as much EPA as ARA.

120. Infant formula according to claim 111 or 112, wherein the fungal oil comprises essentially no EPA.

121. Infant formula according to claim 112, wherein the fungal oil comprises at least 40% ARA.

122. Infant formula according to claim 112, wherein the fungal oil comprises about 50% ARA.

123. Infant formula according to claim 111 or 112, wherein the Mortierella biomass is harvested after culturing and dried using fluid bed drying or spray drying prior to recovery of the fungal oil.

124. A refined fungal triglyceride oil comprising about 32% ARA in the triglyceride, about 4.6% fatty acid 14:0, about 16% fatty acid 16:0, about 3.2% fatty acid 16:1, about 26.4% fatty acid 18:1, about 9.9% fatty acid 18:2, about 4.1% fatty acid 18:3, about 2.2% fatty acid 20:1, and about 1.4% fatty acid 20:3, wherein fungal oil comprises essentially no EPA.

125. Fungal oil in accordance with claim 124, wherein the fungal oil is produced by a species of Mortierella.

126. Fungal oil in accordance with claim 125, wherein the Mortierella is M. alpina.

127. A method of providing triglyceride containing ARA to an infant formula which comprises adding a refined fungal oil to an infant formula in an amount sufficient to provide an ARA content which corresponds to the amount of ARA in human breast milk, the fungal oil comprising about 32 % ARA in the form of triglyceride, about 4.6% fatty acid 14:0, about 16% fatty acid 16:0, about 3.2% fatty acid 16:1, about 26.4% fatty acid 18:1, about 9.9% fatty acid 18:2, about 4.1% fatty acid 18:3, about 2.2% fatty acid 20:1, and about 1.4% fatty acid 20:3, wherein the fungal oil comprises essentially no EPA.

128. The method in accordance with claim 127, wherein the fungal oil is produced by a species of Mortierella.

129. The method in accordance with claim 128, wherein the Mortierella is M. alpina.

130. A method of providing a human with supplemental arachidonic acid (ARA) comprising administering to a human in need of supplemental ARA a composition containing refined fungal oil, the fungal oil comprising about 32% ARA in the form of triglyceride, about 4.6% fatty acid 14:0, about 16% fatty acid 16:0, about 3.2% fatty acid 16:1, about 26.4% fatty acid 18:1, about 9.9% fatty acid 18:2, about 4.1% fatty acid 18:3, about 2.2% fatty acid 20:1, and about 1.4% fatty acid 20:3, wherein the fungal oil comprises essentially no EPA and is present in an amount effective to provide supplemental ARA to said human.

131. The method in accordance with claim 130, wherein the fungal oil is produced by a species of Mortierella.

132. The method in accordance with claim 131, wherein the Mortierella is M. alpina.

* * * * *

(12) EX PARTE REEXAMINATION CERTIFICATE (8695th)
United States Patent
Kyle

(10) Number: US 5,658,767 C2
(45) Certificate Issued: Nov. 22, 2011

(54) ARACHIDONIC ACID AND METHODS FOR THE PRODUCTION AND USE THEREOF

(75) Inventor: David J. Kyle, Catonsville, MD (US)

(73) Assignee: Martek Biosciences Corporation, Columbia, MD (US)

Reexamination Request:
No. 90/009,686, Mar. 18, 2010

Reexamination Certificate for:
| Patent No.: | 5,658,767 |
| Issued: | Aug. 19, 1997 |
| Appl. No.: | 08/367,881 |
| Filed: | Jan. 3, 1995 |

Reexamination Certificate C1 5,658,767 issued May 18, 2010

Related U.S. Application Data

(63) Continuation-in-part of application No. 08/202,878, filed on Feb. 28, 1994, now abandoned, which is a continuation of application No. 08/065,507, filed on May 24, 1993, now abandoned, which is a continuation of application No. 07/645,454, filed on Jan. 24, 1991, now abandoned.

(51) Int. Cl.
| A23C 9/152 | (2006.01) |
| A23C 9/20 | (2006.01) |
| A23C 11/04 | (2006.01) |
| A23D 9/00 | (2006.01) |
| A23D 9/007 | (2006.01) |
| A23L 1/29 | (2006.01) |
| A23L 1/30 | (2006.01) |
| A61K 8/36 | (2006.01) |
| A61K 8/37 | (2006.01) |
| A61K 8/92 | (2006.01) |
| A61K 8/96 | (2006.01) |
| A61K 8/99 | (2006.01) |
| A61K 31/20 | (2006.01) |
| A61K 31/202 | (2006.01) |
| A61K 31/23 | (2006.01) |
| A61K 31/232 | (2006.01) |
| A61P 3/06 | (2006.01) |
| A61P 17/00 | (2006.01) |
| A61P 25/00 | (2006.01) |
| A61Q 19/00 | (2006.01) |
| A61Q 19/08 | (2006.01) |
| C11B 1/00 | (2006.01) |
| C11B 1/10 | (2006.01) |
| C11C 3/00 | (2006.01) |

(52) U.S. Cl. .................. 435/134; 426/585; 514/558; 514/560

(58) Field of Classification Search ................ None
See application file for complete search history.

(56) References Cited

To view the complete listing of prior art documents cited during the proceeding for Reexamination Control Number 90/009,686, please refer to the USPTO's public Patent Application Information Retrieval (PAIR) system under the Display References tab.

*Primary Examiner*—Evelyn Huang

(57) ABSTRACT

The present invention relates to processes for the production of arachidonic acid containing oils, which preferably are substantially free of eicosapentaneoic acid. The invention also relates to compositions containing such oils, in an unmodified form, and to uses of such oils. In a preferred embodiment, Pythium insidiosum is cultivated, harvested and the oil is extracted, recovered, and used as an additive for infant formula. In an alternative embodiment, Mortierella alpina is cultivated, harvested and the oil is extracted, recovered, and used as an additive for infant formula.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 19-31, 42 and 48-52 were previously cancelled.

Claims 43-46 are cancelled.

Claims 14 and 16 are determined to be patentable as amended.

Claims 15, 17 and 18, dependent on an amended claim, are determined to be patentable.

Claims 1-13, 32-41, 47 and 53-132 were not reexamined.

14. A method for the production of an arachidonic acid-containing oil, said oil containing triglycerides wherein at least 25% of the fatty acid residues are ARA, and the amount of EPA residues in the oil is no more than one-fifth the amount of ARA residues, comprising (a) cultivating Mortierella sp. in an aerated fermentor containing culture medium having a carbon source in an amount equivalent to at least 80 g/L glucose and a nitrogen source in an amount equivalent to at least 15 g/L yeast extract;

(b) [maintaining] *adjusting the pH in two or more steps, such that* the pH *is maintained* between 5 and 6 at the beginning of the cultivation[;] *during the exponential growth phase, and* [(c) maintaining] the pH *is maintained* between 7 and 7.5 at the end of the cultivation *during the stationary phase*; and

[(d)] (*c*) harvesting biomass from the fermentor and recovering said arachidonic acid-containing oil from said biomass.

16. The method of claim 14 or 15 wherein the Mortierella sp. is M. alpina.

\* \* \* \* \*

(12) EX PARTE REEXAMINATION CERTIFICATE (9816th)
United States Patent
Kyle

(10) Number: US 5,658,767 C3
(45) Certificate Issued: Aug. 27, 2013

(54) ARACHIDONIC ACID AND METHODS FOR THE PRODUCTION AND USE THEREOF

(75) Inventor: David J. Kyle, Catonsville, MD (US)

(73) Assignee: DSM IP Assets B.V., Heerlen (NL)

Reexamination Request:
No. 90/009,981, Jan. 4, 2012

Reexamination Certificate for:
Patent No.: 5,658,767
Issued: Aug. 19, 1997
Appl. No.: 08/367,881
Filed: Jan. 3, 1995

Reexamination Certificate C1 5,658,767 issued May 18, 2010

Reexamination Certificate C2 5,658,767 issued Nov. 22, 2011

Related U.S. Application Data

(63) Continuation-in-part of application No. 08/202,878, filed on Feb. 28, 1994, now abandoned, which is a continuation of application No. 08/065,507, filed on May 24, 1993, now abandoned, which is a continuation of application No. 07/645,454, filed on Jan. 24, 1991, now abandoned.

(51) Int. Cl.
| | |
|---|---|
| *A23D 9/00* | (2006.01) |
| *A23C 11/00* | (2006.01) |
| *A23C 11/04* | (2006.01) |
| *A23L 1/30* | (2006.01) |
| *A23L 1/29* | (2006.01) |
| *A61K 8/92* | (2006.01) |
| *A61K 31/21* | (2006.01) |
| *A61K 31/232* | (2006.01) |
| *A61K 31/202* | (2006.01) |
| *A61K 31/185* | (2006.01) |
| *A61Q 19/00* | (2006.01) |
| *C12P 7/64* | (2006.01) |
| *C11B 1/10* | (2006.01) |

(52) U.S. Cl.
USPC .......................................................... 435/134

(58) Field of Classification Search
None
See application file for complete search history.

(56) References Cited

To view the complete listing of prior art documents cited during the proceeding for Reexamination Control Number 90/009,981, please refer to the USPTO's public Patent Application Information Retrieval (PAIR) system under the Display References tab.

*Primary Examiner* — Evelyn Huang

(57) ABSTRACT

The present invention relates to processes for the production of arachidonic acid containing oils, which preferably are substantially free of eicosapentaneoic acid. The invention also relates to compositions containing such oils, in an unmodified form, and to uses of such oils. In a preferred embodiment, Pythium insidiosum is cultivated, harvested and the oil is extracted, recovered, and used as an additive for infant formula. In an alternative embodiment, Mortierella alpina is cultivated, harvested and the oil is extracted, recovered, and used as an additive for infant formula.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 124-132 is confirmed.
Claims 19-31, 42-46 and 48-52 were previously cancelled.
Claims 53-123 are cancelled.
Claims 1-18, 32-41 and 47 were not reexamined.

\* \* \* \* \*